(12) United States Patent
Schwartz et al.

(10) Patent No.: US 11,724,030 B2
(45) Date of Patent: Aug. 15, 2023

(54) METHOD AND APPARATUS FOR DIAGNOSIS AND TREATMENT OF MICROVASCULAR DYSFUNCTION

(71) Applicant: CorFlow Therapeutics AG, Baar (CH)

(72) Inventors: Robert S. Schwartz, Inver Grover Heights, MN (US); Jon Helge Hoem, Baar (CH); Martin T. Rothman, Santa Rosa, CA (US)

(73) Assignee: CorFlow Therapeutics AG, Baar (CH)

( * ) Notice: Subject to any disclaimer, the term of this patent is extended or adjusted under 35 U.S.C. 154(b) by 806 days.

(21) Appl. No.: 16/577,962

(22) Filed: Sep. 20, 2019

(65) Prior Publication Data
US 2020/0093991 A1     Mar. 26, 2020

Related U.S. Application Data

(60) Provisional application No. 62/734,364, filed on Sep. 21, 2018.

(51) Int. Cl.
*A61M 5/172*    (2006.01)
*A61B 5/00*    (2006.01)
(Continued)

(52) U.S. Cl.
CPC ......... *A61M 5/1723* (2013.01); *A61B 5/6853* (2013.01); *A61M 5/142* (2013.01);
(Continued)

(58) Field of Classification Search
CPC ........... A61B 2017/00022; A61B 2017/00084; A61B 2017/00243; A61B 2017/22051;
(Continued)

(56) References Cited

U.S. PATENT DOCUMENTS

| | | |
|---|---|---|
| 4,689,041 A | 8/1987 | Corday et al. |
| 6,156,005 A | 12/2000 | Theron |

(Continued)

FOREIGN PATENT DOCUMENTS

| | | |
|---|---|---|
| AU | 2017205404 A1 | 7/2018 |
| CA | 3010447 A1 | 7/2017 |

(Continued)

OTHER PUBLICATIONS

"International Application Serial No. PCT US2019 021426, International Search Report dated Jul. 3, 2019", 4 pages.

(Continued)

*Primary Examiner* — Jason E Flick
(74) *Attorney, Agent, or Firm* — Eversheds Sutherland (US) LLP; Christopher C. Bolten; Regis C. Worley, Jr.

(57) ABSTRACT

Methods and devices for the diagnosis and treatment of microvascular dysfunction, such as microvascular obstruction (MVO) and other dysfunctional diseases of the microvasculature of many organs, including the heart. The present subject matter provides novel devices and methods to successfully diagnose, restore patency, open and preserve flow, and limit reperfusion injury in organs and cases with microvascular dysfunction. The present subject matter provides apparatus and method to detect, measure and treat microvascular dysfunction in real time during scenarios such as invasive angiographic/therapeutic procedures. Such procedures include therapy for organ systems including the heart (acute myocardial infarction—primary percutaneous coronary intervention (PPCI)), brain stroke (CVA), bowel ischemia/infarction, pulmonary emboli/infarction, critical limb ischemia/infarction, renal ischemia/infarction, and others. The present subject matter provides various systems including an infusion and sensing catheter, diagnostic agents, therapeutic agents, and a control console with specialized (Continued)

algorithms to diagnose and treat microvascular dysfunction, such as MVO, in real-time with real-time operator feedback for interventional procedures.

20 Claims, 15 Drawing Sheets

(51) Int. Cl.
  *A61M 5/142* (2006.01)
  *A61M 25/00* (2006.01)
  *A61B 17/22* (2006.01)
(52) U.S. Cl.
  CPC ............. *A61M 25/007* (2013.01); *A61B 2017/22051* (2013.01); *A61B 2017/22084* (2013.01); *A61M 2005/1726* (2013.01); *A61M 2230/30* (2013.01)
(58) Field of Classification Search
  CPC .......... A61B 2017/22054; A61B 2017/22067; A61B 2017/22084; A61B 2090/064; A61B 5/02007; A61B 5/0215; A61B 5/6853; A61B 5/283; A61M 2005/1726; A61M 2205/3331; A61M 2205/502; A61M 2230/30; A61M 25/007; A61M 5/1408; A61M 5/142; A61M 5/16827; A61M 5/172; A61M 5/1723; A61M 5/168; A61M 2205/33; A61M 5/16804
  See application file for complete search history.

(56) References Cited

U.S. PATENT DOCUMENTS

| | | | |
|---|---|---|---|
| 6,295,990 B1 | 10/2001 | Lewis et al. |
| 6,423,032 B2 | 7/2002 | Parodi |
| 6,485,500 B1 | 11/2002 | Kokish et al. |
| 6,488,671 B1 | 12/2002 | Constantz et al. |
| 7,722,596 B2 | 5/2010 | Shapland et al. |
| 7,837,650 B1 | 11/2010 | Cox et al. |
| 8,177,704 B1 | 5/2012 | Mohl et al. |
| 8,366,659 B2 | 2/2013 | Ehrenreich et al. |
| 8,430,861 B2 | 4/2013 | Schwartz et al. |
| 8,540,669 B2 | 9/2013 | Ehrenreich et al. |
| 8,708,996 B2 | 4/2014 | Consigny et al. |
| 8,876,850 B1 | 11/2014 | Vollmers et al. |
| 9,174,020 B2 | 11/2015 | Allen et al. |
| 9,205,226 B2 | 12/2015 | Allen |
| 9,320,846 B2 | 4/2016 | Burns et al. |
| 9,433,381 B2 | 9/2016 | Mohl et al. |
| 9,433,761 B2 | 9/2016 | Schwartz et al. |
| 9,550,046 B1 | 1/2017 | Allen et al. |
| 9,844,383 B2 | 12/2017 | Allen |
| 9,855,049 B2 | 1/2018 | Schiemanck et al. |
| 9,999,718 B2 | 6/2018 | Brady et al. |
| 10,118,016 B2 | 11/2018 | Schwartz et al. |
| 10,315,016 B2 | 6/2019 | Schwartz et al. |
| 10,952,883 B2 | 3/2021 | Hoem et al. |
| 11,135,408 B2 | 10/2021 | Schwartz et al. |
| 2001/0041862 A1 | 11/2001 | Glickman |
| 2004/0260333 A1 | 12/2004 | Dubrul et al. |
| 2005/0049451 A1 | 3/2005 | Schock et al. |
| 2005/0245894 A1 | 11/2005 | Zadno-Azizi |
| 2005/0245897 A1 | 11/2005 | Bolduc et al. |
| 2005/0267561 A1 | 12/2005 | Jones et al. |
| 2008/0300573 A1 | 12/2008 | Consigny et al. |
| 2009/0177183 A1 | 7/2009 | Pinkernell et al. |
| 2010/0168649 A1 | 7/2010 | Schwartz et al. |
| 2010/0249704 A1 | 9/2010 | Wagner |
| 2010/0280451 A1 | 11/2010 | Teeslink et al. |
| 2011/0196255 A1 | 8/2011 | Kassab |
| 2012/0157913 A1 | 6/2012 | Aziz et al. |
| 2012/0265079 A1 | 10/2012 | Hilmersson |
| 2012/0265283 A1 | 10/2012 | Mack et al. |
| 2013/0035560 A1 | 2/2013 | Anand et al. |
| 2013/0165858 A1 | 6/2013 | Cox et al. |
| 2015/0133799 A1 | 5/2015 | O'Connell et al. |
| 2015/0141853 A1 | 5/2015 | Miller, III et al. |
| 2016/0082178 A1 | 3/2016 | Agah et al. |
| 2016/0199003 A1 | 7/2016 | McCaffrey et al. |
| 2016/0213834 A1 | 7/2016 | Brady et al. |
| 2016/0270731 A1 | 9/2016 | Burkett |
| 2016/0361068 A1 | 12/2016 | Mohl et al. |
| 2017/0189654 A1* | 7/2017 | Schwartz .............. A61M 5/142 |
| 2017/0290598 A1 | 10/2017 | Culbert et al. |
| 2018/0185576 A1 | 7/2018 | Burns et al. |
| 2018/0280172 A1 | 10/2018 | Hoem et al. |
| 2018/0353681 A1 | 12/2018 | Burmaster et al. |
| 2019/0046760 A1 | 2/2019 | Schwartz et al. |
| 2019/0082976 A1 | 3/2019 | Hoem et al. |
| 2019/0275248 A1 | 9/2019 | Schwartz et al. |
| 2019/0358437 A1 | 11/2019 | Schwartz et al. |
| 2020/0282189 A1 | 9/2020 | Gaynor |
| 2020/0383688 A1 | 12/2020 | Olson et al. |
| 2021/0228387 A1 | 7/2021 | Hoem et al. |
| 2021/0361170 A1 | 11/2021 | Schwartz et al. |
| 2021/0366620 A1 | 11/2021 | Bernard et al. |

FOREIGN PATENT DOCUMENTS

| | | |
|---|---|---|
| CN | 201058169 Y | 5/2008 |
| CN | 103826690 A | 5/2014 |
| CN | 108778149 A | 11/2018 |
| EP | 3399923 A1 | 11/2018 |
| EP | 3399923 A4 | 8/2019 |
| GB | 2541368 A | 2/2017 |
| JP | 2006187620 A | 7/2006 |
| JP | 2013146505 A | 8/2013 |
| JP | 2016168151 A | 9/2016 |
| JP | 2019502522 A | 1/2019 |
| WO | WO-9600596 A1 | 1/1996 |
| WO | WO-0128419 A2 | 4/2001 |
| WO | WO-0170325 A2 | 9/2001 |
| WO | WO-2004062526 A2 | 7/2004 |
| WO | WO-2006059317 A1 | 6/2006 |
| WO | WO-2008088579 A2 | 7/2008 |
| WO | WO-2014106158 A1 | 7/2014 |
| WO | WO-2015108928 A1 | 7/2015 |
| WO | 2017004432 | 1/2017 |
| WO | WO-2017078693 A1 | 5/2017 |
| WO | WO-2017120229 A1 | 7/2017 |
| WO | 2017160270 | 9/2017 |
| WO | WO-2018175485 A1 | 9/2018 |
| WO | WO-2019060421 A1 | 3/2019 |
| WO | 2019173758 | 9/2019 |
| WO | WO-2019232452 A1 | 12/2019 |

OTHER PUBLICATIONS

"International Application Serial No. PCT US2019 021426, Written Opinion dated Jul. 3, 2019", 5 pages.

"International Application Serial No. PCT US2019 052245, International Search Report dated Nov. 27, 2019", 4 pages.

"International Application Serial No. PCT US2019 052245, Written Opinion dated Nov. 27, 2019", 8 pages.

Costa, et al., "Mimicking Arterial Thrombosis in a 3d-printed Microfluidic in Vitro Vascular Model Based on Computed Tomography Angiography Data," Lab on a Chip, Royal Society of Chemistry, 17(16):2785-2792 (Jun. 2017).

Extended European Search Report dated Jul. 19, 2019 in EP Patent Appl. Serial No. 17736254.8 (0130).

International Search Report & Written Opinion dated Apr. 7, 2022 in Int'l PCT Patent Appl. Serial No. PCT/IB2022/050152 (0810).

International Search Report & Written Opinion dated Aug. 9, 2021 in Int'l PCT Patent Appl. Serial No. PCT/IB2021/054453 (0710).

International Search Report and Written Opinion dated Jan. 3, 2019 in Int'l PCT Patent Application Serial No. PCT/US2018/051760 (0310).

International Search Report and Written Opinion dated Mar. 17, 2017 in Int'l PCT Patent Application Serial No. PCT/US2017/012181 (0110).

(56) References Cited

OTHER PUBLICATIONS

International Search Report and Written Opinion dated May 25, 2018 in Int'l PCT Patent Application Serial No. PCT/US2018/023422 (0210).

International Search Report and Written Opinion dated Oct. 1, 2019 in Int'l PCT Patent Application Serial No. PCT/US2019/035020 (0510).

Lindsey, et al., "Guidelines for Experimental Models of Myocardial Ischemia and Infarction," American Journal of Physiology—Heart and Circulatory Physiology, 314(4):H812-H838 (Apr. 2018).

Liu, JingHua, Coronary Heart Disease: Anatomy, Function and Imaging, Peking Union Medical College Press, Apr. 30, 2013, p. 56.

Qiu, et al., "Microvasculature-on-a-Chip for the Long-term Study of Endothelial Barrier Dysfunction and Microvascular Obstruction in Disease," Nature Biomedical Engineering, 2(6):453-463 (Apr. 2018).

Supplementary European Search Report dated Apr. 24, 2020 in EP Patent Appl. Serial No. 18771178.3 (0230).

Tsai, et al., "In Vitro modeling of the microvascular occlusion and thrombosis that occur in hematologic diseases using microfluidic technology," Journal of Clinical Investigation, 122(1):408-418 (Jan. 2012).

U.S. Appl. No. 15/398,470, filed Jan. 4, 2017.
U.S. Appl. No. 15/926,911, filed Mar. 20, 2018.
U.S. Appl. No. 16/135,987, filed Sep. 19, 2018.
U.S. Appl. No. 16/297,339, filed Mar. 8, 2019.
U.S. Appl. No. 16/413,436, filed May 15, 2019.
U.S. Appl. No. 16/577,962, filed Sep. 20, 2019.
U.S. Appl. No. 17/000,240, filed Aug. 21, 2020.
U.S. Appl. No. 17/059,190, filed Nov. 25, 2020.
U.S. Appl. No. 17/207,194, filed Mar. 19, 2021.
U.S. Appl. No. 17/327,433, filed May 21, 2021.
U.S. Appl. No. 17/491,430, filed Sep. 30, 2021.
U.S. Appl. No. 17/647,546, filed Jan. 10, 2022.
U.S. Appl. No. 16/297,339, filed Mar. 8, 2019, System for Diagnosing and Treating Microvascular Obstructions.

* cited by examiner

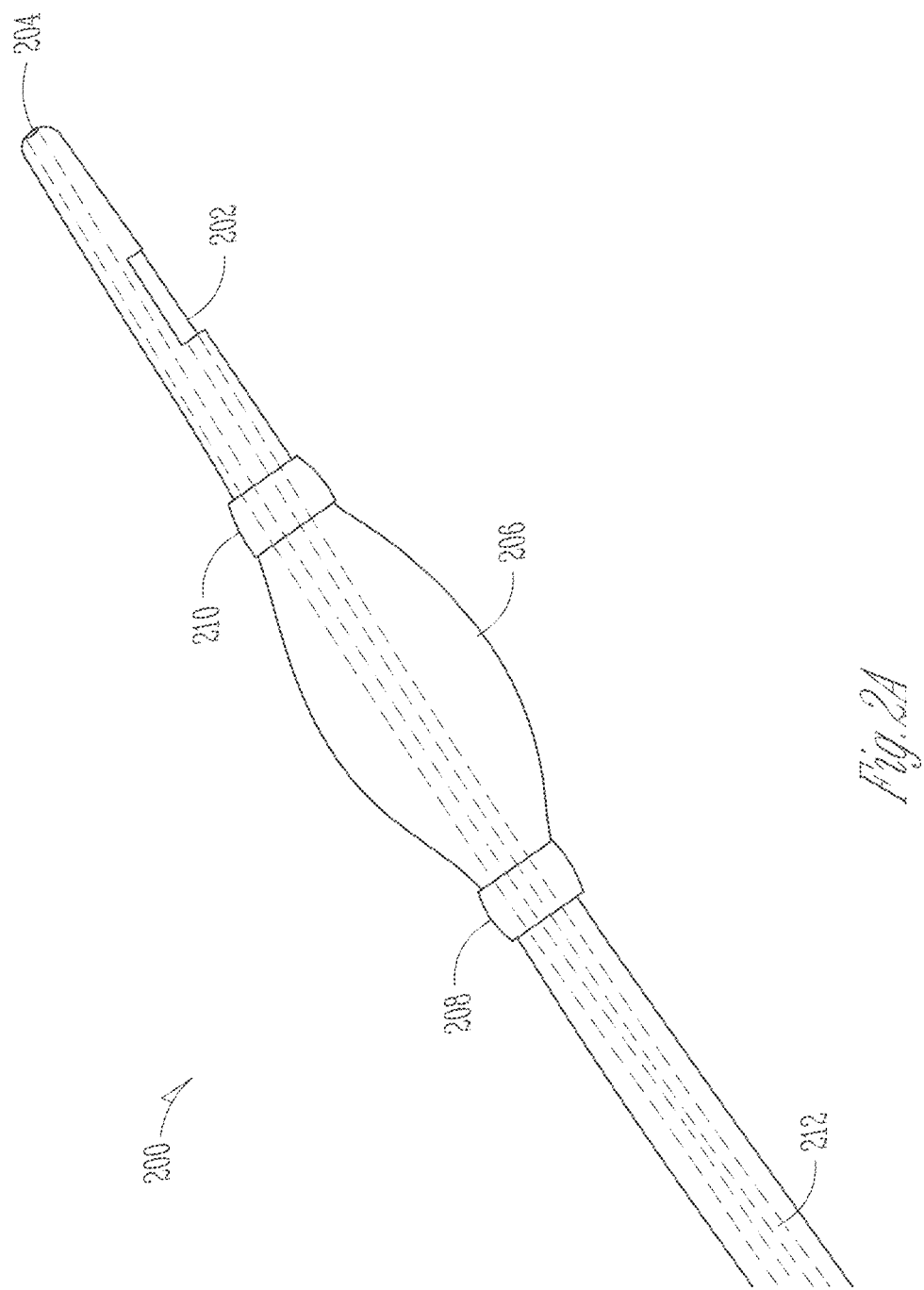

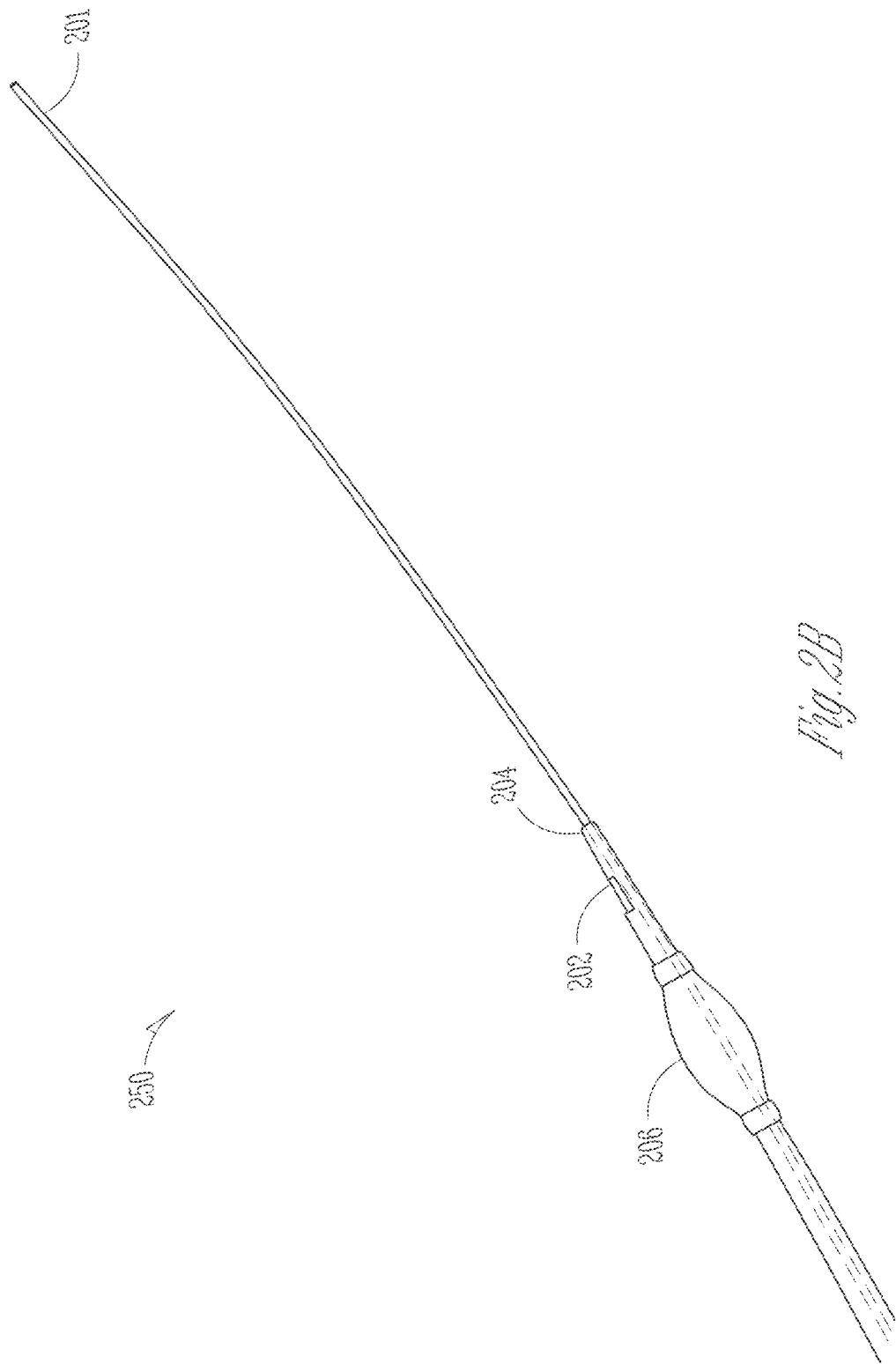

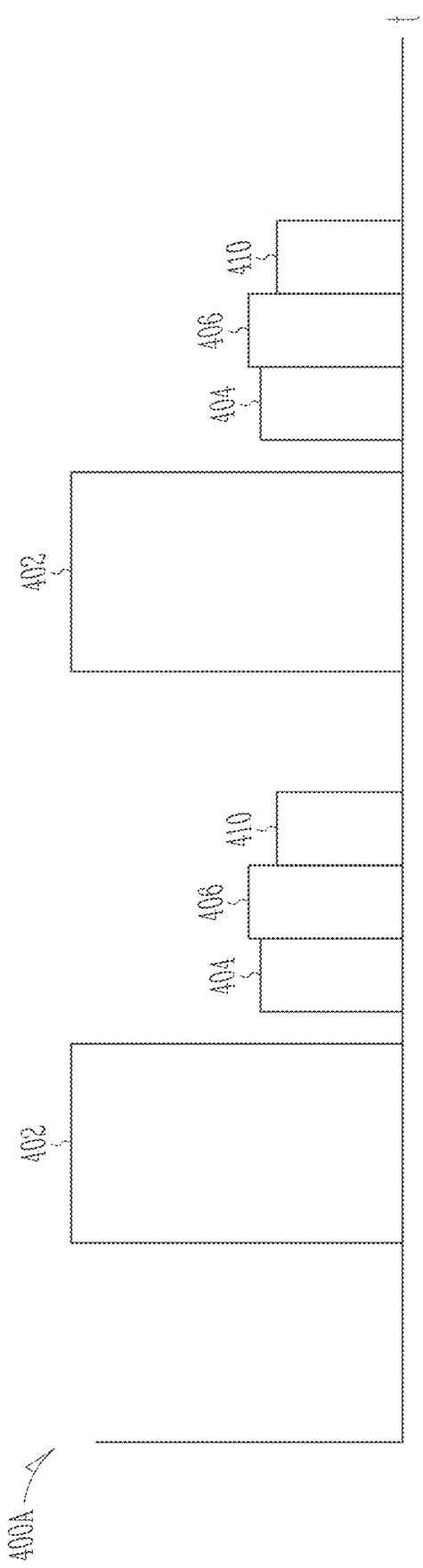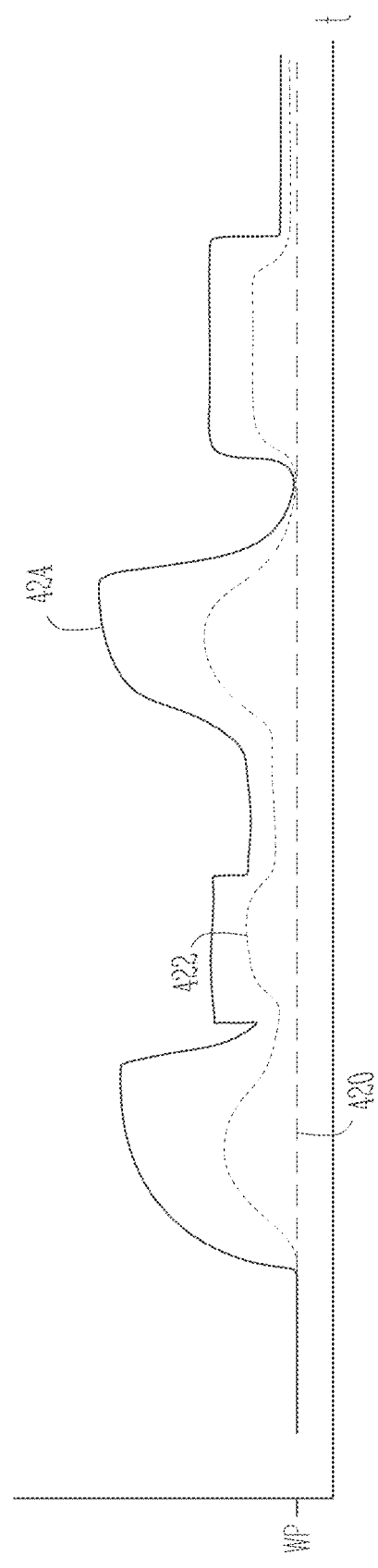

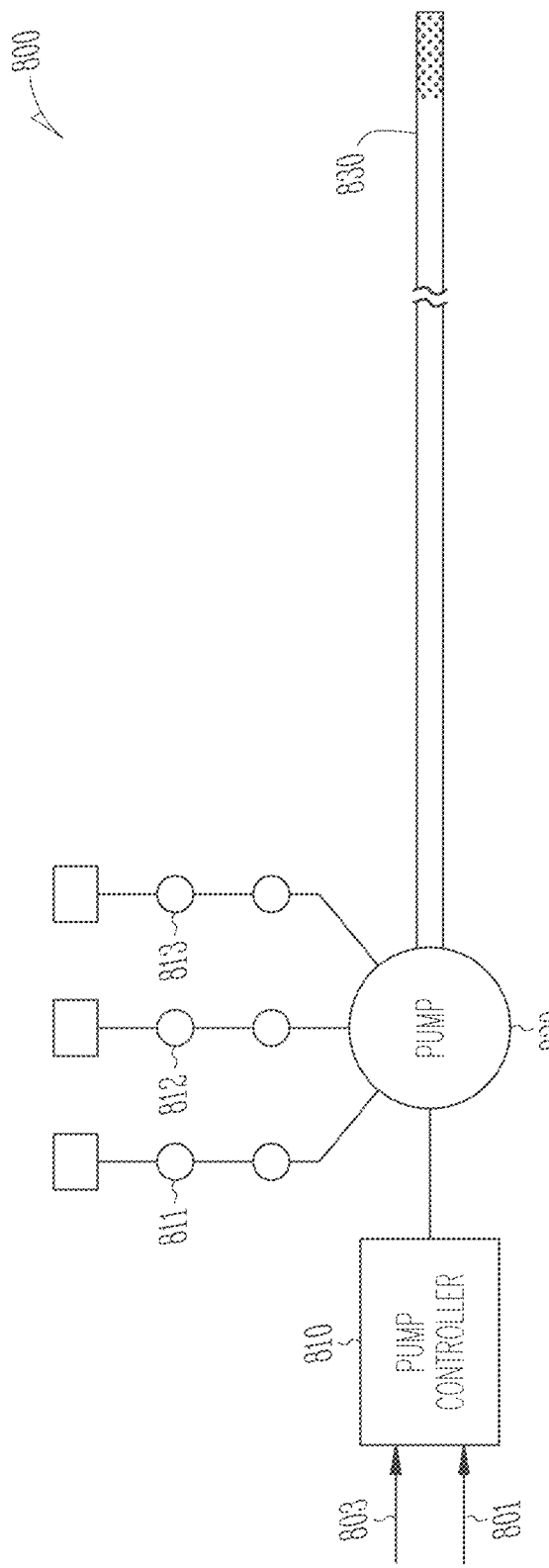

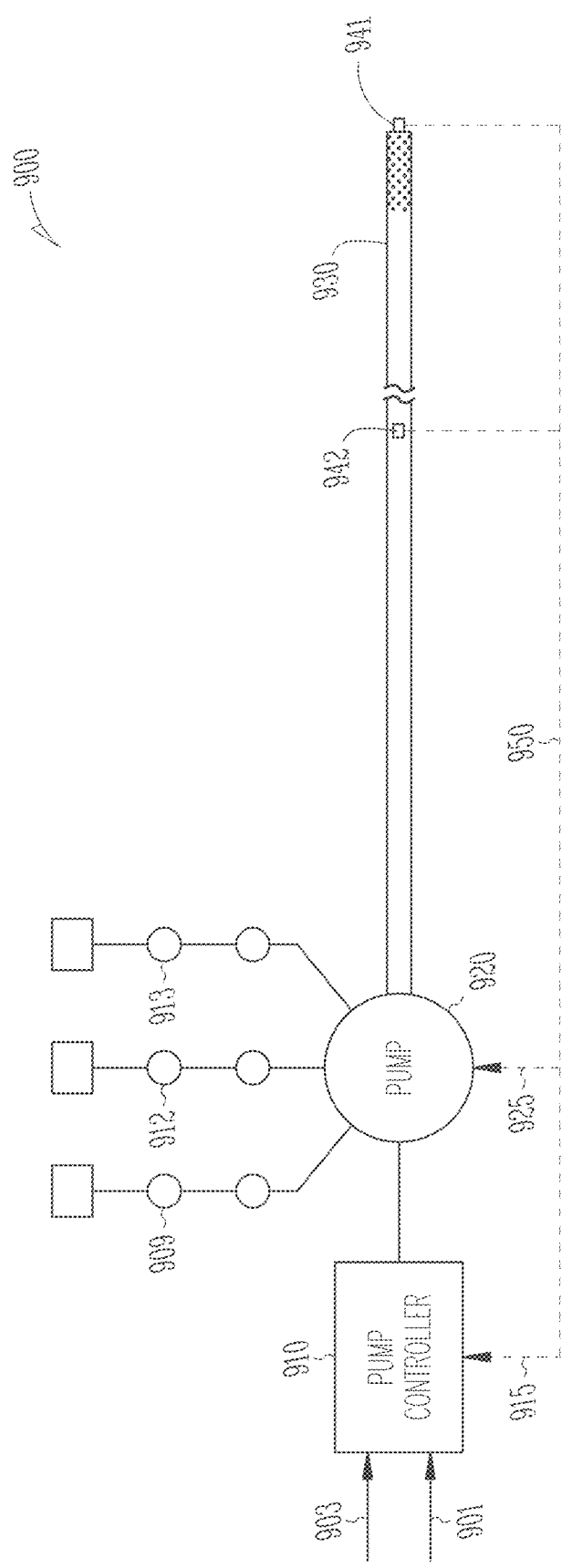

METHOD AND APPARATUS FOR DIAGNOSIS AND TREATMENT OF MICROVASCULAR DYSFUNCTION

CLAIM OF PRIORITY AND RELATED APPLICATIONS

This application claims the benefit under 35 U.S.C. 119(e) of U.S. Provisional Ser. No. 62/734,364, filed Sep. 21, 2018, which is hereby incorporated by reference in its entirety.

This application is related to:

U.S. patent application Ser. No. 15/398,470, filed Jan. 4, 2017, published as US 2017/0189654 A1 Jul. 6, 2017, and which claims the benefit of: U.S. Provisional Ser. No. 62/274,744 filed Jan. 4, 2016; U.S. Provisional Ser. No. 62/320,230 filed Apr. 8, 2016; U.S. Provisional Ser. No. 62/358,433 filed Jul. 5, 2016; and U.S. Provisional Ser. No. 62/379,074 filed Aug. 24, 2016; and PCT Patent Application Ser. No. PCT/US17/12181 published as WO02017120229A1 on Jul. 13, 2017, which claims priority to all of the aforementioned patent applications; and U.S. Provisional Patent Application Ser. No. 62/560,545, filed Sep. 19, 2017; and U.S. Provisional Patent Application Ser. No. 62/640,932 filed Mar. 9, 2018, all of which are collectively referred to as the "Incorporated Applications." All of the Incorporated Applications are hereby incorporated by reference in their entirety.

TECHNICAL FIELD

Methods and devices for the diagnosis and treatment of microvascular dysfunction (MVD) and other diseases of the microvasculature of many organs, including the heart.

BACKGROUND

Heart attack or STEMI ('STEMI' defined as acute ECG ST segment myocardial infarction) is caused by sudden occlusion of an epicardial coronary artery, typically by fibrin and platelet rich clot, with associated embolic plaque and debris. Electrocardiographic signs of acute transmural myocardial infarction (heart attack) are ST segment elevation (STEMI) in multiple anatomic leads. ST segment elevation is a hallmark of severe coronary artery occlusion or narrowing, causing ischemic myocardial injury and cell death. Large vessel occlusion is often associated with small vessel stenosis occlusion (termed microvascular occlusion or MVO) by hemodynamic collapse, clot with embolic debris and other effects which cause reduced blood supply. MVO is an independent predictor of late adverse events including death and heart failure, without successful therapy to date.

Interventional cardiology is proficient at opening severely narrowed or occluded epicardial coronary arteries in the cardiac catheterization laboratory using catheters, guide wires, balloons, and stents. However, microvascular obstruction cannot be diagnosed nor treated in the catheter laboratory. Importantly, MVO cannot be treated even if/when it could be accurately diagnosed.

Heart muscle salvage (saving muscle from death due to ischemia/lack of blood and oxygen) is a critical concern to ensure good long-term outcomes in patients suffering STEMI. A key component of good long-term outcome involves minimizing the time between coronary artery occlusion (at home or outside the hospital) and opening the occluded artery in the catheter laboratory. Interventional cardiologists can reduce artery occlusion time by implementing streamlined and efficient emergency medical systems whose goal is to bring STEMI patients to the catheterization laboratory as soon as possible, avoiding long term STEMI complications. Complications resulting from STEMI and MVO include systolic and diastolic heart failure, arrhythmias, aneurysms, ventricular rupture and multiple other serious complications. These complications can markedly shorten life and impose severe limitations on quality of life.

Modern interventional therapy for acute myocardial infarction has matured over time with impressive clinical results. Heart attack/STEMI death rates at 30 days have dropped from more than 30% to less than 5%, achieved by reperfusing the heart with blood as soon as possible after coronary arterial occlusion. This goal is accomplished by streamlining clinical care systems to open coronary arteries in the catheterization lab as rapidly as possible after heart attack onset. Emergency procedures including stenting and balloon angioplasty are undisputed as necessary for improving early and late clinical results of acute heart attack therapy.

However, substantial challenges remain for treating STEMI patients and reducing long term complications. These problems include heart failure (poor cardiac function and cardiac enlargement), cardiac/ventricular rupture, persistent ischemic chest pain/angina, left ventricular aneurysm and clot, and malignant arrhythmias.

Late heart failure complicates 25-50% of STEMI, and consists of poor left ventricular function and damaged myocardium. Heart failure is worsened as the heart remodels in shape and size with associated functional loss. Nearly half of all new heart failure in patients under 75 years is linked to STEMI.

Many years investigating STEMI therapy show that opening the epicardial/large coronary artery is insufficient to salvage heart muscle and optimize long term patient outcomes. A very common reason for poor late results after heart attack is microvascular obstruction (MVO) MVO is occlusion or severe flow limitation in the internal cardiac microvessels. These microvessels are impervious to stenting and conventional thrombolytic therapy due to their size and number. Thus, despite widely patent epicardial coronary arteries, residual MVO obstructs blood flow into the heart causing cell ischemia and death and resulting in severe long term heart muscle damage.

MVO thus remains a critical frontier in cardiology. Cardiac microvessels comprise small arteries, arterioles, capillaries and venules which are frequently collapsed and filled with cells, clot and debris (platelets, fibrin, and embolic plaque material) during STEMI. Too often, obstructed microvessels (MVO) do not resolve even after stent placement and have serious long-term negative prognostic implications.

MVO is very common in STEMI patients, even though stenting and balloon angioplasty are successful at opening epicardial coronary arteries. MVO occurs in more than half of all STEMI patients, even with good blood flow through open the epicardial arteries and newly placed stents.

MVO extent is key to the severity of myocardial damage and patient outcome. MVO is best imaged via cardiac MRI which measures MVO location, extent and severity. MRI, however, cannot be performed emergently or during a cardiac catheterization procedure since it requires patients to be in a separate imaging area and within a large, separate MRI scanner.

Important features of MVO may be summarized by the following:

1. MVO and microvascular dysfunction in STEMI is the principal cause of major complications early and late after heart attack.
2. Angiographic "no-reflow" or "low-reflow" is caused by MVO and is due to obstructed microvessels within the heart. MVO in severe cases is fluoroscopically characterized by very slow radiographic contrast filling the epicardial coronary arteries as visualized during coronary treatment in the catheterization laboratory. Radiographic contrast filling, however, is only able to diagnose the severe no-reflow cases and thus is not able to detect the majority of the patients with MVO.
3. MVO causes myocardial cell injury and death from prolonged ischemia/lack of oxygen, blood, and key metabolic nutrients such as glucose. MVO microscopic analysis shows collapsed microvessels with red cells, platelet and fibrin clot, dead myocardial cells, inflammatory cells, myocyte cell death, and endothelial cell death along the obstructed intramyocardial capillaries.
4. MVO studied acutely shows cardiac arterioles and capillaries completely occluded by platelet and fibrin-rich thrombus, platelet-neutrophil aggregates, dying blood cells and embolic debris.
5. When MVO complicates acute STEMI/myocardial infarction, far greater heart/myocardial damage occurs, and poor ventricular function occurs early.
6 MVO is very common. It occurs in.
 a. 53% of all STEMI and NSTEMI regardless of epicardial flow.
 b. 90% of Large Transmural STEMI,
 c. 40% of MI with TIMI III (normal) X-ray visualized flow, and
 d. MVO is the single most potent prognostic marker of events after controlling for infarct size
7. Patients with microvascular obstruction have more late major adverse cardiovascular events (MACE) than those without MVO (45% versus 9%)
8. MVO is the best predictor of acute and chronic cardiovascular adverse outcomes.
9. MVO acutely becomes late fibrous scar and causes poor cardiac function.

MVO cannot be diagnosed in a conventional catheterization laboratory. Moreover, no effective conventional therapies were available. Many possible prior therapies all proved essentially ineffective, and in some cases, dangerous.

A major complication from myocardial infarction is cell death or ischemia. Myocardial infarction may cause short, but profound ischemia, which is reversible ("stunning"), chronic ischemia that occurs when myocardial cells are alive but without sufficient oxygen or nutrients to contract normally ("hibernation"); or necrosis and infarction via prolonged ischemia. It typically spreads as a wave, beginning in endocardium and spreads across the myocardial wall. Each of these events can be characterized by noninvasive imaging and testing such as nuclear, echo, and PET methods. However, an exceptionally good test is provided by cardiac MRI. The use of gadolinium contrast can visualize microvascular obstruction.

Myocardial infarction (MI) resulting in microvascular obstruction (MVO) has profound clinical impact. While epicardial coronary arterial occlusion is well known, it has been hypothesized that microscopic/microvascular plugging by thrombus-platelets and fibrin of the microvasculature also occurs. Histopathologic studies do show limited fibrin and platelet aggregation in both human cases and in animal models. Microvascular plugging also occurs due to red blood cells, white cells and fibrin-platelet aggregates which are not visible to light microscopy may occur, but can only be seen via immunostains and EM/SEM/TEM. To date, heterotopic platelet aggregation is possible but unproven.

However, MVO is only one disorder of several disorders under a larger classification of microvascular dysfunction. Microvascular dysfunction also occurs in patients without epicardial artery occlusion and as such affects a much larger patient group than the acute coronary occlusion (STEMI) patient group. The effects of occlusion of vessels less than 200 microns in diameter in patients without epicardial artery (vessels larger than 2 mm) occlusion are poorly understood despite years of study and many failed therapeutic strategies.

There is therefore a need in the art for apparatus and methods that can assess microvascular function and dysfunction in this larger patient population. Such apparatus and methods may benefit patients by providing an assessment in real-time or near real-time. There is also a need in the art for apparatus and methods that can diagnose and treat microvascular dysfunction, including microvascular obstruction (MVO) and tissue necrosis/infarction. There is further a need for apparatus and methods that permit assessment, diagnosis and treatment of problems in real time or near real-time, permit treatment decisions, and/or allow real time estimation of microvascular injury and ongoing treatment efficacy.

SUMMARY

Methods and apparatus for the real time or near real time assessment, diagnosis and treatment of microvascular dysfunction. In various embodiments, the microvascular dysfunction includes clinical syndromes such as STEMI/NSTEMI, microvascular obstruction (MVO), no-reflow, cardiogenic shock, and other dysfunctional diseases of the microvasculature. The present subject matter is applicable to diagnosis and treatment of many organs including the heart. More particularly, non-limiting embodiments include novel devices and methods to successfully diagnose, restore patency, open and preserve flow, and limit reperfusion injury in organs and cases with microvascular dysfunction. Applications include but are not limited to therapy for organ systems including the heart (acute myocardial infarction—primary percutaneous coronary intervention (PPCI)), brain (stroke (CVA), bowel ischemia/infarction, pulmonary emboli/infarction, critical limb ischemia/infarction, renal ischemia/infarction, liver, peripheral vascular, neurovascular and others.

Using various embodiments of the present subject matter, a system comprising specialized infusion and sensing catheter, diagnostic agents, therapeutic agents, and control console with specialized algorithms can be used to both diagnose and treat microvascular dysfunction in general, and the diseases falling in that classification, such as MVO, by eliminating the microvascular clot and debris causing the narrowing and/or obstruction. The techniques include various embodiments whereby a combination of novel devices, methods, and software to simultaneously diagnose and treat microvascular dysfunction, such as MVO. The present subject matter permits operation in real-time with real-time operator feedback for diagnostic and therapeutic decision making, and so create a system capable of performing interventional procedures.

Systems and apparatus are included that are configured to perform microvascular function assessment. In various embodiments, such assessment is done in real time. Systems and apparatus are also included in various embodiments to diagnose and treat microvascular dysfunction, such as microvascular obstruction (MVO). In various embodiments, the system and apparatus allow for real time diagnosis and treatment using invasive, catheterization methods. In various embodiments, the present subject matter provides controlled coronary flow infusion (CoFI) as a catheter-based technique capable of accurate, continuous microvascular function assessment in real time. Studies were performed using CoFI to explore STEMI effects on microvasculature function.

Methods for treatment of microvascular obstruction in an organ using a defined flow infusion to a site, and pressure measurement of the resulting superposition of infused and native fluids are provided. These methods include applying a first fluid pulse at defined, elevated pressures and/or flows to open microvessels, and then applying a defined flow of infusate at defined pressures/flows, which typically (but not necessarily) are lower than the elevated pressure to treat the microvascular obstruction and to reduce, avoid or eliminate ischemia and necrosis of organ tissue. The present disclosure also provides various catheter designs for delivery of infusates, drugs, and/or other fluids and medicines while at the same time providing a controllable flow/pressure to the vessel or organ under diagnosis and treatment. Open and closed loop delivery apparatus and method are provided which can provide customized diagnosis and treatment of tissues by adjusting variables such as the injectate pressure, flow, concentration, oxygenation, mixture of native blood flow to infusate, among other things. The system is also programmable to provide feedback to control flow, pressure, intracoronary ECG and/or other variables. The system is also programmable to be timed to a patient's cardiac rhythm for a number of different diagnosis and therapy options.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

BRIEF DESCRIPTION OF THE DRAWINGS

The present disclosure is illustrated by way of example and not limitation in the figures of the accompanying drawings, in which like references indicate similar elements and in which:

FIGS. 2A-2B illustrate an example of an infusion catheter having an occlusion balloon, in accordance with some embodiments of the present subject matter;

FIGS. 4A-4B illustrate a graph of an infusion sequence, in accordance with some embodiments of the present subject matter;

FIG. 8 shows an open loop block diagram of a system for delivery of the preparatory pulse and following pulses/infusions according to one embodiment of the present subject matter;

FIG. 9 shows a closed loop block diagram of a system for delivery of the preparatory pulse and following pulses/infusions according to one embodiment of the present subject matter;

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present subject matter includes devices, systems and methods for unique techniques for measuring dynamic Microvascular Resistance (dMVR) to assess, diagnose and treat microvascular dysfunction, such as STEMI/NSTEMI, microvascular obstruction (MVO), no-reflow, cardiogenic shock, and other dysfunctional diseases of the microvasculature. The present subject matter is applicable to diagnosis and treatment of many organs, including the heart. More particularly, non-limiting embodiments include novel devices and methods to successfully diagnose, restore patency, open and preserve flow, and limit reperfusion injury in organs and cases with microvascular dysfunction. Applications include but are not limited to therapy for organ systems including the heart (acute myocardial infarction—primary percutaneous coronary intervention (PPCI)), brain (stroke (CVA), bowel ischemia/infarction, pulmonary emboli/infarction, critical limb ischemia/infarction, renal ischemia/infarction, liver, peripheral vascular, neurovascular and others obstruction (MVO) and tissue necrosis/infarction.

Figure 1:
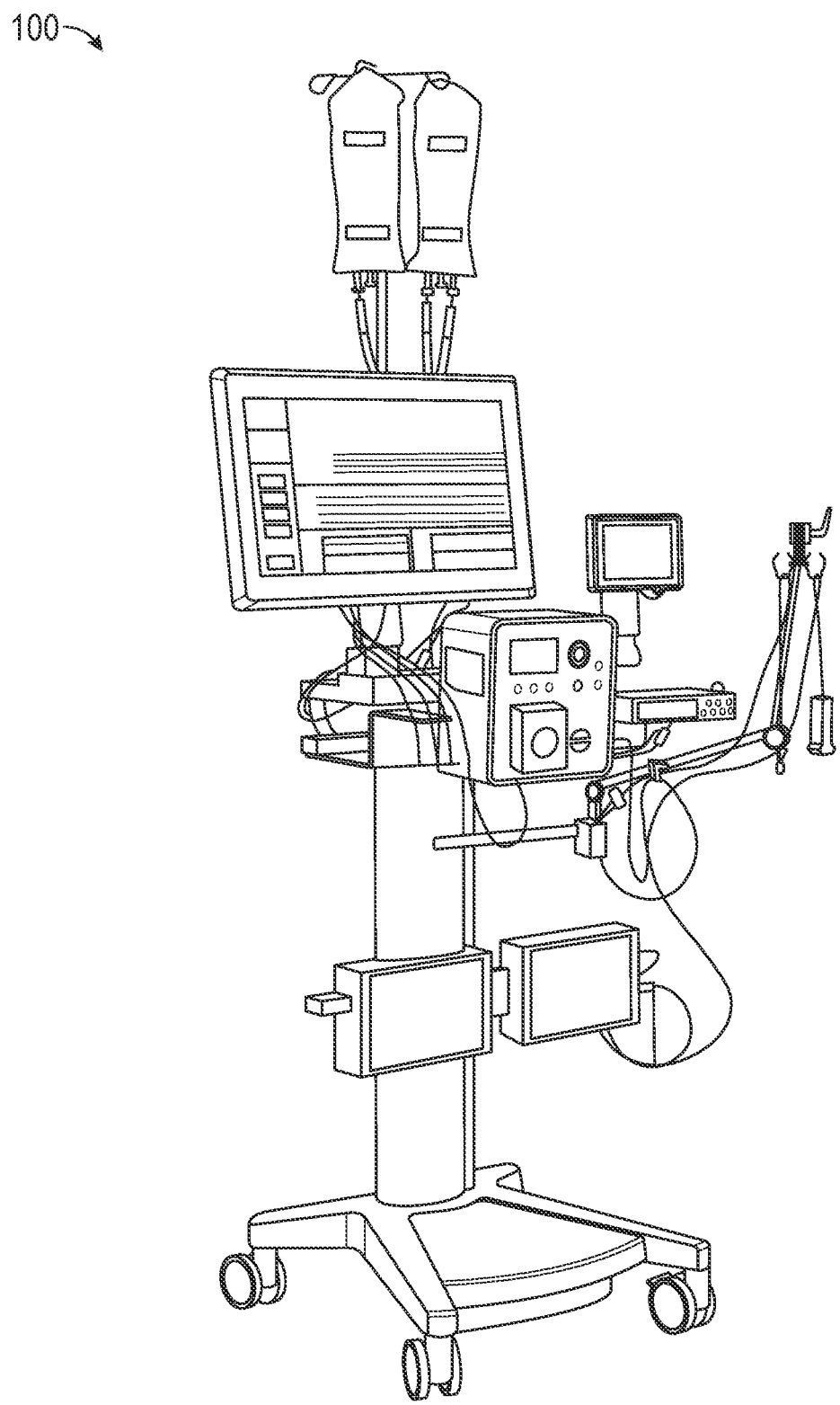
FIG. 1 illustrates an example of a modular computerized diagnostic and infusion system for coronary and other human/animal vasculature; in accordance with some embodiments of the present subject matter.

FIG. 1 illustrates an example of a modular computerized diagnostic and infusion system 100 (hereinafter "infusion system") for coronary and other human/animal vasculature and organs; in accordance with some embodiments of the present subject matter. The infusion system 100 can be a clinical ready modular system and can be configured in a mobile console form. The infusion system 100 can enable direct measurement and diagnosis of microvascular dysfunction, including MVO and other microvascular abnormalities by:

real-time coronary artery pressure and flow;
pressure/resistance time parameters;
Waterfall Pressure or Coronary Wedge or Coronary artery Residual Pressure;
intracoronary electrocardiography (ECG); and/or
fractional flow reserve (FFR) measurements in the epicardial arteries.

The infusion system 100 can enable therapy by:
infusion of approved agent(s);
targeted, controlled and low flow infusion; and/or
continuous monitoring of diagnostic parameters.

FIG. 2A illustrates an example 200 of an infusion catheter having an occlusion balloon 206, balloon markers 208 and 210, and infusion port 202 in fluid communication with an infusion lumen 212 in accordance with some embodiments of the present subject matter. Guidewire lumen 204 is provided so that the infusion catheter can be slid along a guidewire to a desired position.

FIG. 2B illustrates an example 300 of an infusion catheter 250 having an occlusion balloon 206 placed over a 0.014" pressure measuring guidewire 201 in a rapid-exchange (RX) fashion, in accordance with some embodiments of the present subject matter. In the example shown, the catheter 250 can slide over a guidewire 201 via guidewire lumen 204. Infusion port 202 can deliver fluids via infusion lumen 212 while guidewire 201 is disposed in lumen 204.

Figure 3A:
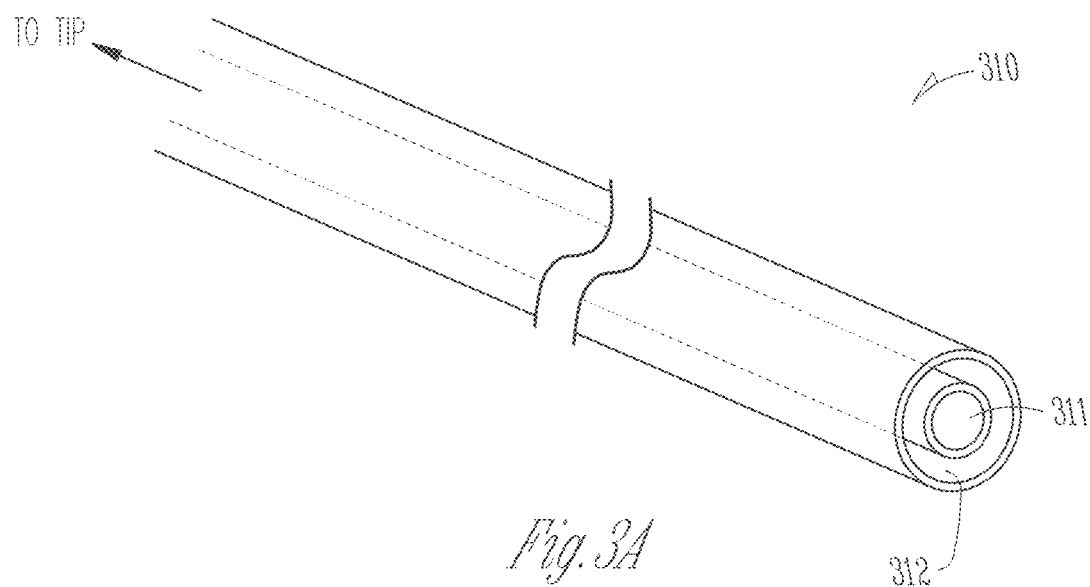
FIG. 3A illustrates an example of a central portion of an infusion catheter, in accordance with some embodiments of the present subject matter.

FIG. 3A illustrates an example of a central portion of an infusion catheter 310, in accordance with some embodiments of the present subject matter. The central portion shows a cross section with an infusion lumen 312 encircling a guidewire lumen 311. It is understood that in various embodiments, the infusion lumen may be side-by-side or may be in a nonlinear path about the guidewire lumen. Other configurations are possible. One aspect is to provide a small cross sectional area to allow the catheter to be introduced into smaller vessels for therapy.

Figure 3B:
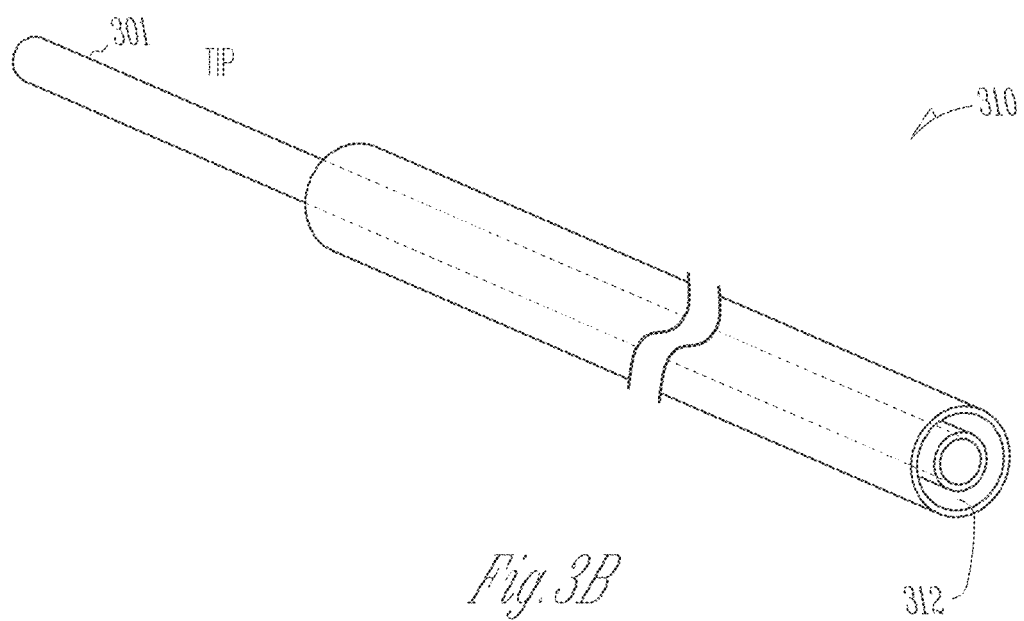
FIG. 3B illustrates an example of a distal portion of an infusion catheter, in accordance with some embodiments of the present subject matter.

FIG. 3B illustrates an example of a distal portion of an infusion catheter, in accordance with some embodiments of the present subject matter. In this embodiment, the guidewire 301 exits the distal portion of the catheter and can be used for placement of the catheter in the proper anatomical location. In embodiments where the guide wire also provides pressure sensing, the guidewire can be positioned outside or within the catheter lumen to provide various pressure sensing at the distal end of the catheter in situ.

Figure 3C:
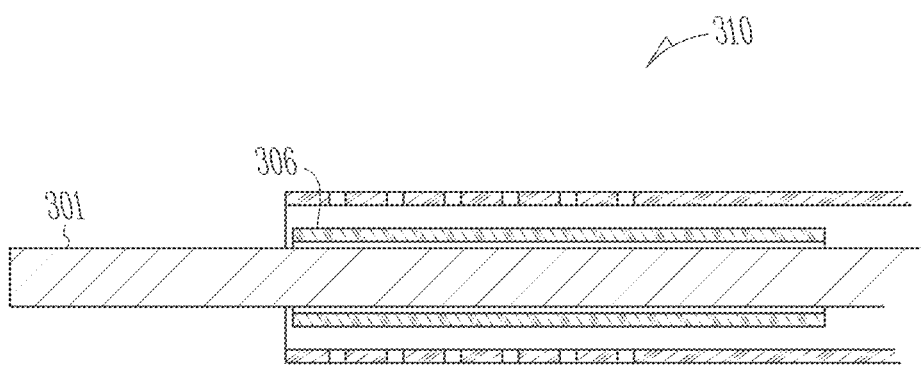
FIG. 3C illustrates an example of a distal portion of an infusion catheter having a pressure chamber, in accordance with some embodiments of the present subject matter.

FIG. 3C illustrates an example of a distal portion of an infusion catheter having a pressure chamber 306, in accordance with some embodiments of the present subject matter. The pressure chamber is designed to provide a region of stable pressure measurement in the distal arterial segment. It is an integral component of the device holding the guidewire 301 and permits pressure measurement at locations different than near or distal to the catheter tip.

Figure 3D:
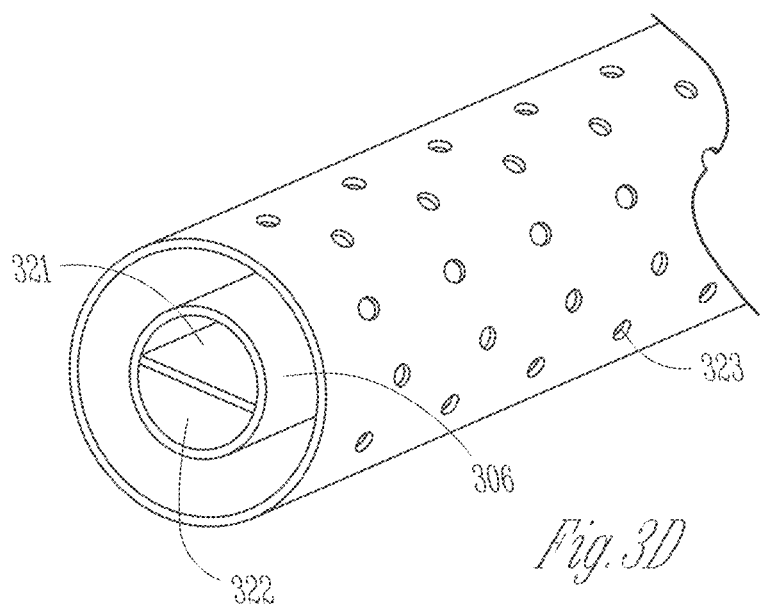
FIG. 3D illustrates an example cross section of a distal portion of an infusion catheter having a pressure chamber, in accordance with some embodiments of the present subject matter.

FIG. 3D illustrates an example cross section of a distal portion of an infusion catheter having a pressure chamber, in accordance with some embodiments of the present subject matter. In various embodiments, the pores or slits or slots 323 provided by the design provide both for better dispersion of infusate at the distal end of the catheter and also more precise pressure measurement. Such pores, slits, or slots 323 can also be patterned to provide an infusate flow pattern desired for a particular therapy. In various embodiments, different lumen configurations may be used, such as lumens 321 and 322, which can be used for guidewire lumens, infusion lumens, or other lumen and port applications.

Figure 5A:
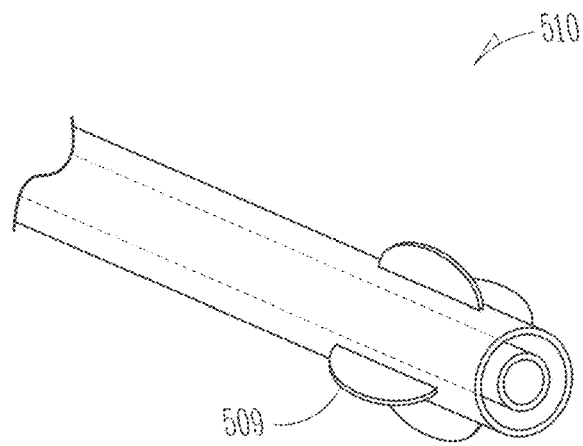
FIG. 5A illustrates a distal portion of an infusion catheter including hemodynamic vanes or fins to urge centering of the distal portion of the catheter in the vessel or organ in which flow is measured, in accordance with some embodiments of the present subject matter.

FIG. 5A illustrates a distal portion of an infusion catheter including hemodynamic vanes or fins 509 to facilitate centering of the distal portion of the catheter in the vessel or organ in which flow is measured, in accordance with some embodiments of the present subject matter. Hydrodynamic forces are symmetric and facilitate centering of the catheter distal end within a flow field.

Figure 5B:
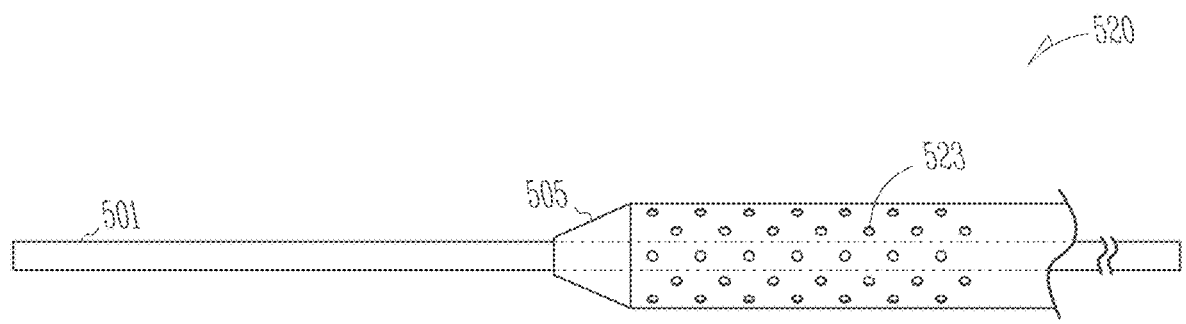
FIG. 5B illustrates a distal portion of an infusion catheter including holes for infusate to be delivered in the vessel or organ in which flow is measured, in accordance with some embodiments of the present subject matter.

FIG. 5B illustrates a distal portion of an infusion catheter 520 including holes for infusate 523 to be delivered in the vessel or organ in which flow is measured, in accordance with some embodiments of the present subject matter. In various embodiments the front end of the catheter has a taper 505 so that the transition from guidewire 501 to diameter of the catheter is more gradual.

Figure 5C:
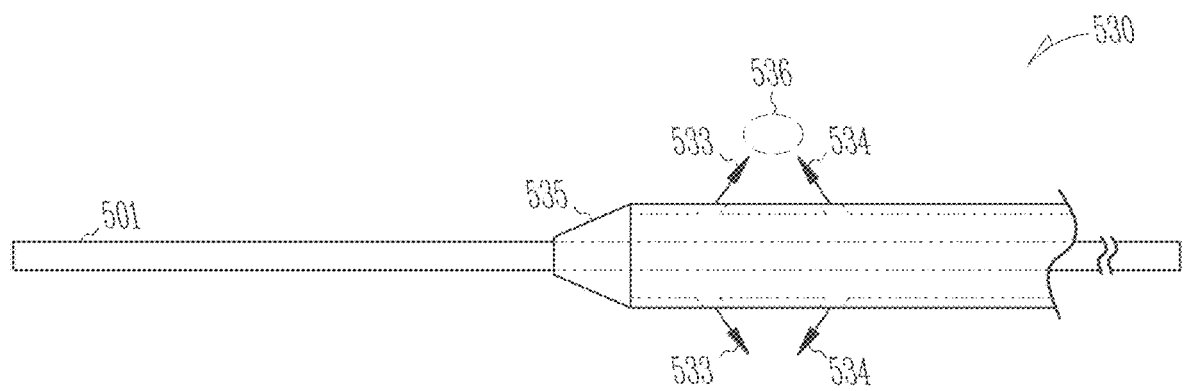
FIG. 5C illustrates a distal portion of an infusion catheter including jets for infusate to be delivered in the vessel or organ in which flow is measured, in accordance with some embodiments of the present subject matter.
Figure 6A:
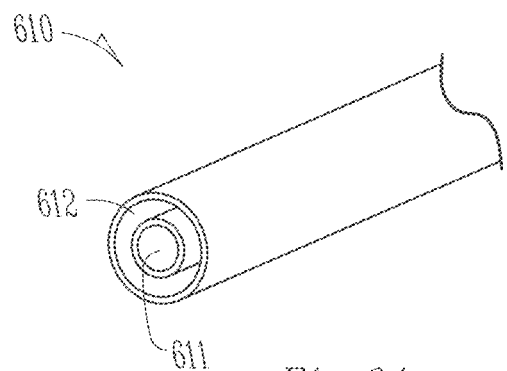
FIGS. 6A-6D illustrate an infusion catheter with coaxial infusion and guidewire lumens, guidewires, infusion holes, and the ability to direct antegrade and retrograde infusate, in accordance with some embodiments of the present subject matter.
Figure 6B:
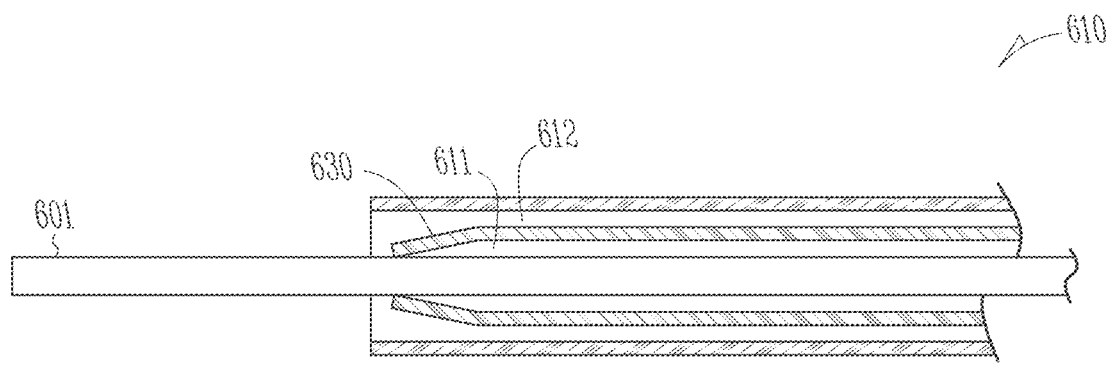
Figure 6C:
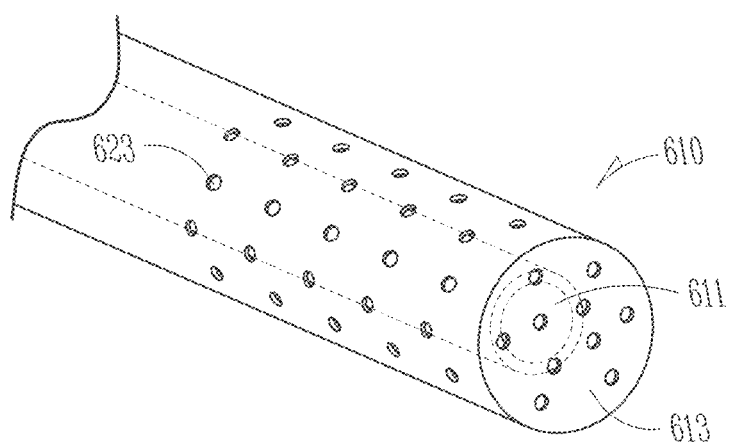
Figure 6D:
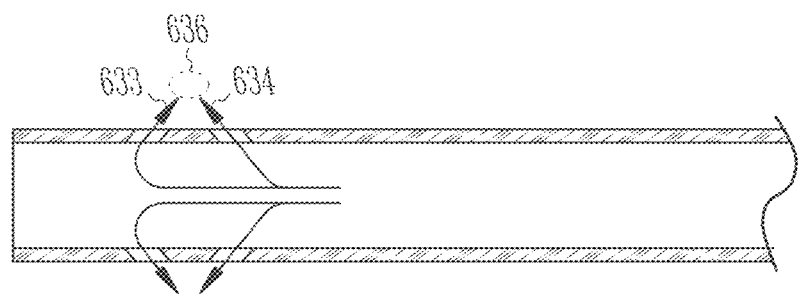

FIG. 5C illustrates a distal portion of an infusion catheter including jets for infusate to be safely delivered in the vessel or organ in which flow is measured, in accordance with some embodiments of the present subject matter. The figure demonstrates that jets can be aimed to provide collision of infusate flow 536 if desired for a particular therapeutic benefit, and their multiplicity will create slower flow and hence lower jet velocity to make vessel dissection of damage lower likelihood. The jets can be retrograde 533 or antegrade 534 jets, in various combinations. In various embodiments the front end of the catheter has a taper 535 so that the transition from guidewire 501 to diameter of the catheter is more gradual.

FIGS. 6A-6D illustrate an infusion catheter 610 with coaxial infusion lumen 612 and guidewire lumen 611, guidewires, infusion holes 623, and a cap 613. The design can direct antegrade 634 and retrograde 633 infusate, in accordance with some embodiments of the present subject matter. The resulting flows can be combined to provide a high flow zone 636.

Figure 7A:
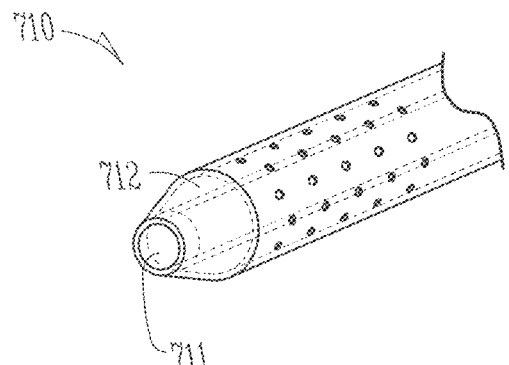
FIGS. 7A-7E illustrate an infusion catheter with coaxial infusion and guidewire lumens, pressure sensor, integrated intra-coronary ECG electrode, and infusion holes, in accordance with some embodiments of the present subject matter.
Figure 7B:
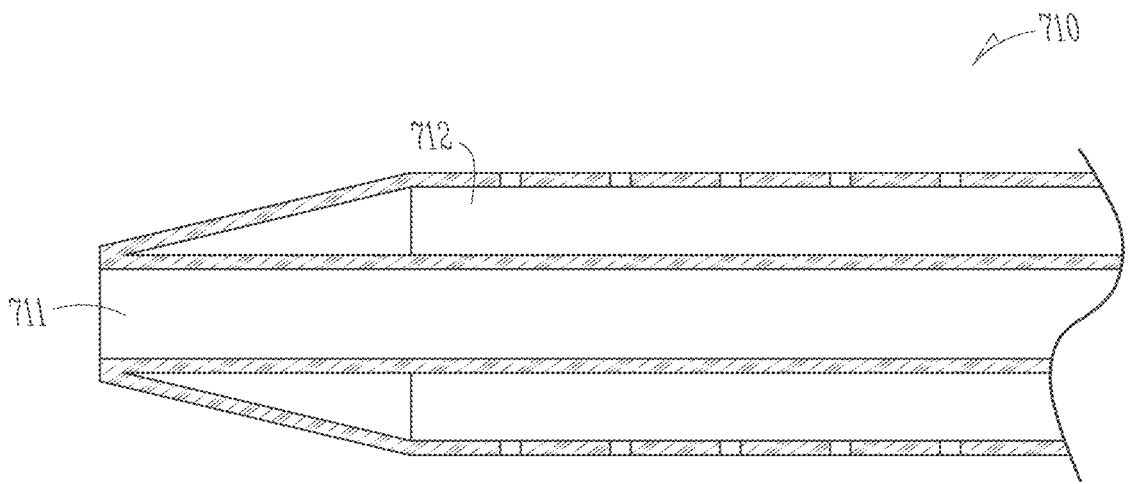
Figure 7C:
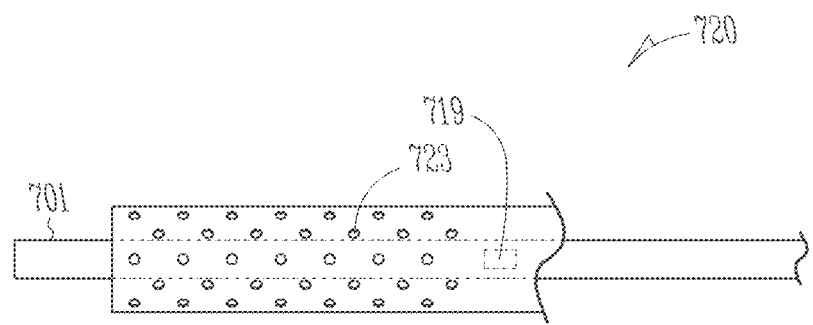
Figure 7D:
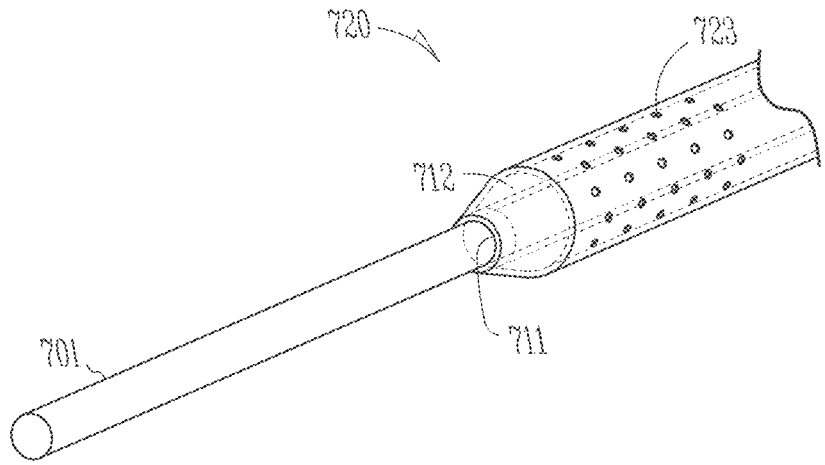
Figure 7E:
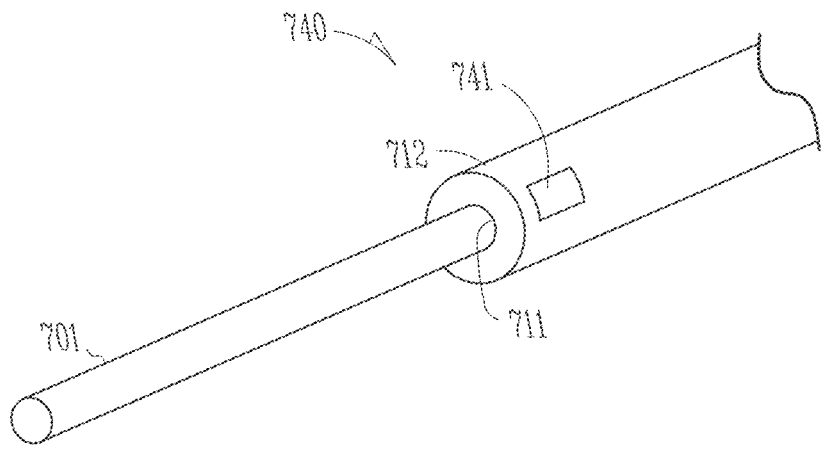

FIGS. 7A-7E illustrate an infusion catheter with coaxial infusion and guidewire lumens, pressure sensor, integrated intra-coronary ECG electrode, and infusion holes, in accordance with some embodiments of the present subject matter. FIG. 7A shows a design 710 having a central lumen 711 surrounded by an infusion lumen 712 in a coaxial configuration. In various embodiments the central lumen may be employed to receive a guidewire 701. In various embodiments, the guidewire may be pressure sensing with a sensor 719. Although the example of FIG. 7A is coaxial, it is understood that the lumens may be configured differently, such as side-by-side. Therefore, variations in cross section and dimensions are possible without departing from the scope of the present subject matter. FIG. 7C shows a guidewire lumen portion of a catheter where a pressure sensing guidewire 701 is able to be used to deploy the catheter. The guidewire may be retracted to perform pressure sensing. In various embodiments, the guidewire lumen may include pressure ports to facilitate sensing of infusion pressure. Sensing of infusion pressure may be made with different sensing configurations, such as a pressure transducer 719 at or near the distal end of the catheter 720, at or near the proximal end of the catheter, and/or at other locations along the catheter. In various embodiments, the guidewire lumen or guidewire may be used for intra-coronary ECG sensing or measurement. FIG. 7D shows a portion of an infusion catheter including an infusion lumen and a guidewire lumen with a guidewire extending from the guidewire lumen. FIG. 7E shows a portion of an infusion catheter 740 with an ECG electrode 741 for sensing ECG signals. In various embodiments, the ECG electrode is integrated into the catheter to obtain intra-coronary ECG signals. In various embodiments, the various sensing aspects of the infusion catheter can be combined, so as to provide various sensing functions by the same infusion catheter. For example, the catheter may include both pressure sensing and ECG sensing, among other things. Therefore, the present subject matter is demonstrated by these embodiments, but is not restricted to the particular combinations shown.

The infusion catheters as shown in FIGS. 2-3 and 5-7 can be used in systems/devices/methods described herein to controllably occlude a desired vessel, infuse desired fluids and measure pressure inside the vessel in real time and distal to the occlusion balloon. The infusion catheters as shown in FIGS. 2-3 and 5-7 can include: a 6F guide sheath compatible catheter, a compliant 5×10 mm occlusion balloon, and can be received over 0.014" pressure guide wire. The infusion catheters as shown in FIGS. 2-3 can include a wide flow infusion range, for example, 5-50 ml/min and can include axial flow infusion.

In some embodiments, the catheter can be inserted into a myocardial vessel supplying blood to a patient's myocardium. In some embodiments, the myocardial vessel or nearby vessels may or may not include microvascular dysfunction, such as MVO and may or may not include myocardial infarction. The catheter can controllably block antegrade blood flow within the myocardial vessel around the catheter by inflating a balloon. In some embodiments, the myocardial vessel can include a stent and the catheter can block antegrade blood flow from within the stent, by inflating a balloon.

FIGS. 4A-4B illustrate a graph 400 of an occlusion and infusion algorithm, in accordance with some embodiments of the present subject matter. In various embodiments, the infusion algorithm is generated by modular computerized infusion system 100 such as is shown in FIG. 1. The infusion system 100 can perform diagnosis of the vessel as set forth in the Incorporated Applications, including, but not limited to, that set forth in U.S. Provisional Patent Application Ser. No. 62/560,545 filed Sep. 19, 2017, which is incorporated by reference in its entirety.

The system provides an initial flow or pressure pulse, a "preparatory pulse" 402 which may include infusate at a higher flow or pressure and of variable temporal duration to inflate, open, or otherwise clear channels of the microvasculature which has obstructive debris and has collapsed. The system thereafter provides pulses of similar or possibly smaller pulse amplitudes (404, 406, 410, etc.) to provide therapeutic infusion to the vessel or organ, as described herein.

The pressures, numbers of steps, pulses and times of infusion can be varied within the scope of the present disclosure. An example of a pressure response is shown in FIG. 4B, where the line 420 is the waterfall pressure (WP) which is the baseline pressure of the tissue under treatment. Curves 422 and 424 show the variation in applied pressure and applied pressure with blood flow due to application of the pulses in FIG. 4A. Flow improves over the course of the applied therapeutic pulses.

FIG. 8 shows an open loop block diagram 800 for delivery of the preparatory pulse and following pulses/infusions according to one embodiment of the present subject matter. In the open loop configuration, flow or pressure pulses are infused at fixed or predetermined parameters. In various embodiments, the pump controller 810 receives inputs (e.g., 801, 803) to perform algorithmic control of the pump and the delivered infusate or infusates (e.g., 811,812, and/or 813 of FIG. 8). The infusates are delivered to the infusion lumen of the infusion catheter 830. In various embodiments, the system can control the infusate delivery, including the type, pressure, flow, dose, temperature, and other parameters of the infusate. In various embodiments, the system can control pressure and inflation of one or more occlusion balloon(s). In various embodiments, the system can control multiple aspects of the system, such as infusate and balloon parameters, among other things.

FIG. 9 shows a closed loop block diagram 900 for delivery of the preparatory pulse and following pulses/infusions according to one embodiment of the present subject matter. In this configuration infusion pressure, flows, volumes or rates may be governed in real time or according to measured/sensed vessel parameters including flow, anatomy, pressure, resistance, intracoronary ECG, or similar physiologic measurements. In various embodiments, the pump controller 910 receives inputs (e.g., 901, 903, etc.) from an operator and inputs from one or more feedback signals (950, 925, 915) sensed by one or more sensors (e.g., 930, 941, etc.) to perform closed loop algorithmic control of the pump and the delivered infusate or infusates (e.g., 909, 912, and/or 913 of FIG. 9). The infusates are delivered to the infusion lumen of the infusion catheter 930. Such a design allows feedback from sensed signals to help the controller provide an algorithmically controlled infusate. Such sensors can modify infusion based on physiologic state and/or measured parameters. Some of the parameters sensed include, but are not limited to, pressure, flow, impedance, cardiac cycle, etc. In various embodiments, the system can use the measured parameters to control the infusate delivery, including the type, pressure, flow, dose, temperature, and other parameters of the infusate. In various embodiments, the system can use the measured parameters to control pressure and inflation of one or more occlusion balloon(s). In various embodiments, the system can use the measured parameters to control multiple aspects of the system, such as infusate and balloon parameters, among other things.

Therapy Based on Restoring Microvascular Flow

In the course of investigating microvascular dysfunction, MI and MVO, it has been observed that epicardial coronary artery obstruction causes acute and profound loss of distal pressure, including and especially the intra-myocardial capillaries. Intramural pressure in the contracting ventricle is cyclic with systole-diastole. Capillaries are thus likely close either completely or partially, and open for more than what occurs in the case of normal blood flow and normal blood pressure in the epicardial coronary arteries which feed the microvasculature. This is shown by epicardial flow velocity measurements and in histologic evaluation of acute myocardial infarction which shows capillaries too small to accommodate red blood cells or white blood cells (e.g. less than 10 μm microvasculature diameter), and with interspersed thrombotic elements such as platelets or fibrin. These observations strongly suggest epicardial coronary artery occlusion causes microvasculature hypotension, creating conditions for catastrophic dynamic collapse and partial or complete microvasculature obstruction.

One method to model microvasculature collapse is to perform a hydrodynamic analysis of the microvasculature in myocardial contracting tissue. The law of Laplace governs pressure required to sustain an open capillary:

$$T = P \times R,$$

Where T is the tension in the blood vessel wall (e.g., units of $kg/(s2)$ P is the pressure across the vessel wall (e.g., kPa), and R is the radius of the blood vessel (e.g., mm). From Laplace's equation, it can be observed that as the radius becomes very small, the pressure required to open a close capillary is very large. Further, Poiseulle's Equation provides a way to model resistance to flow: Vessel Resistance (VR) is proportional to (blood viscosity×Length of vessel)/R4.

Therefore, assuming blood viscosity is relatively constant, vascular resistance is inversely proportional to the fourth power of the radius of the vessel. As the vessel radius shrinks by half, the original vascular resistance VRO increases sixteen-fold: $VR = VRO/(0.54) = VRO/(0.0625) = 16$ VRO.

Thus, restoration of blood pressure and blood flow via interventions such as stenting of the coronary arteries do not supply enough pressure to open a closed capillary bed, resulting in the capillaries remaining partially or completely closed with continuing periodic compression/relaxation during the heart cycle. These physiologic disturbances of normal capillary function are key components of microvascular obstruction, chronic capillary occlusion (with slow flow as evidenced by MRI imaging showing very late gadolinium enhancement at infracted sites).

The present subject matter provides a mechanism to open not only epicardial coronary arteries, but also reverse capillary occlusion due to low pressure and also to mitigate thrombus, microvascular spasm, and other causes of low or no-flow in the capillaries resulting in myocardial cell death. Thus, the present subject matter addresses chronic complications of MI and resulting ischemia, congestive heart failure, arrhythmias, ventricular aneurysms, myocardial rupture, poor prognosis, recurrent clinical events and a multiplicity of severe negative cardiac complications. It is further understood that the present subject matter can be applied to other diseases, such as peripheral vascular disease (limbs), stroke (brain), renal failure (kidney) and diseases affecting blood flow to other bodily parts.

Therapeutics

Several therapeutic components of this application include physiologic-biophysical mitigation of microvascular compromise including stenosis, obstruction, inflammation, reperfusion injury, and chronic malfunction. In various embodiments, addition of chemotherapeutic agents infused locally through a coronary artery catheter systemically may be followed for longer time periods by routes such as intravenously. In various embodiments, coronary direct drug infusion becomes a systemic infusion. Several drug classes are described including, but not limited to, antiplatelet agents, acute and chronic Thrombin Inhibitors (both direct and indirect), and vasodilators including nitric oxide donors and stimulators of nitric oxide synthase.

For example, in various embodiments, antiplatelet agents in the form of anti-aggregatory agents such as direct thrombin inhibitors (hirudin and its molecular analogues, platelet receptor inhibitors—GP IIb/IIIa inhibitors; factor X inhibitors; low molecular weight heparin and fibrin inhibitors and fibrin fibrinolytics) are available for use.

Vasodilator drugs may be used for real-time vasodilating microvasculature as lytic therapeutic is infused, which have therapeutic and diagnostic properties. Some examples include nitroglycerin (TNG), low dose dopamine, Adenosine, acetyl choline, Papaverine, hydralazine, calcium channel blockers, and others.

Devices for Therapeutic Infusion

The present subject matter provides various infusion catheters for therapy. In various embodiments a catheter is adapted to receive a guidewire which may have a pressure sensing capability, for delivery of the distal tip of the catheter to a site and to deliver infusate from the proximal end of the catheter to the distal end of the catheter via a lumen. In various embodiments, the infusate is delivered by an infusion lumen. In various embodiments, the catheter includes a guidewire lumen to receive a pressure sensing or standard guidewire.

In certain embodiments, the catheter includes a multiplicity of lumens. In embodiments including an infusion lumen and a guidewire lumen, the infusion lumen and guidewire lumen may be separate and oriented to be adjacent to each other or coaxial to each other. The infusion lumen may be used for drug delivery or for delivery of infusate for diagnostic or therapeutic infusion, or combinations thereof. In various embodiments, the catheter includes a lumen for pressure monitoring either directly or via pressure sensing wire. In various embodiments the lumen for pressure monitoring may receive a pressure sensing guidewire. In various embodiments, the catheter includes dedicated lumens for delivery of infusate and pressure sensing. In various embodiments, the catheter includes dedicated lumens for delivery of infusate, pressure sensing, and for accommodating the guidewire. In various embodiments, the catheter includes dedicated lumens for delivery of infusate, drug delivery, and pressure sensing. In various embodiments, the catheter includes dedicated lumens for delivery of infusate, drug delivery, pressure sensing, and for accommodating the guidewire. Infusate lumina may have holes, slots, or otherwise be able to diffuse flow (diagnostic or therapeutic) for safer injection into blood vessels.

In various embodiments, the catheter includes vanes or fins adapted to urge the catheter away from the walls of the vessel it resides in to provide safer and more consistent pressure measurement. In various embodiments, the vanes or fins are adapted to center the catheter within the vessel it resides in. In various embodiments, the vanes or fins include hydrodynamic qualities adapted to urge the catheter away from the walls of the vessel and/or to center the catheter in vessel.

In various embodiments, shaft design, vanes or fins with hydrodynamic impact may be placed on the surface of the catheter distally to equalize hydrodynamic flow around the catheter and to force a catheter into the central steams of blood flow via the Bernoulli principle.

These vanes may also direct blood into an open chamber at the distal end of the catheter to facilitate accurate pressure measurement in the surrounding artery or vascular structure.

In various embodiments of the catheter, at least a portion of the distal end of the catheter is made more flexible. In various embodiments, flexibility is enhanced by a change in durometer of catheter material, or a pattern of cuts or both. In various embodiments, the cuts are performed so as to make spirals or other patterns for flow diffusion (avoid jetting, for safer injection). In various embodiments the patterns are circles, irregular patterns, all typically made by laser or other micro-machining methods. Differential stiffness can be created by these patterns, or by other methods such as holes a multiplicity of patterns, changing size and density to allow the tip segment to have differential flexibility in a pattern beneficial for tracking but also for admitting blood into the distal pressure chamber.

In various embodiments a plurality of micro holes with changing size, shape, and density allow for variations in catheter tip or proximal component compliance.

In various embodiments, a distal hole or lumen for guidewire insertion and exit through the distal tip of the catheter permits utilizing a pressure guidewire to place the catheter using standard interventional methods, including a "rapid exchange" configuration. When proper placement is achieved the pressure guidewire may be pulled retrograde back to facilitate a pressure sensing mode. The wire is pulled back into a chamber within the catheter body that ensures full exposure to blood pressure though cuts, holes, or slots, because blood or other fluids (such as diagnostic and/or infusates) combined provide accurate pressure measurement.

In various embodiments, the system allows to measure intracoronary ECG either over the guide wire, pressure guide wire or an electrode located on the distal end of the catheter.

In various embodiments, the differential hole pattern may vary longitudinally to not only alter compliance but also to alter resistance to flow of infusates. In this configuration differential exit of flow longitudinally down the catheter can be achieved. In various embodiments, equal exit of flow can be achieved using holes, spirals, and their patterns, which are varied systematically to decrease or increased resistance as a function of longitudinal direction down the axis of the catheter. In various embodiments, the patterns of holes, cuts, and spirals have multi-function of the control relative fluid exit at various pressures and to alter compliance of the distal tip to facilitate catheter steering and tracking over a guidewire which may be a pressure wire to allow distal pressure sensing.

In wire-based embodiments allowing insertion of the guidewire, a distal tip of the catheter may also include a multiplicity of holes, cuts, wedges, spirals or other apertures. In various embodiments, the aperture patterns are chamfered or tilted to force or urge blood into the resulting enclosed chamber.

Additional catheter designs are provided, such as those described in the Incorporated Applications:
U.S. patent application Ser. No. 15/398,470, filed Jan. 4, 2017, published as US 2017 0189654 A1 Jul. 6, 2017, and which claims the benefit of: U.S. Provisional Ser. No. 62/274,744 filed Jan. 4, 2016; U.S. Provisional Ser. No. 62/320,230 filed Apr. 8, 2016; U.S. Provisional Ser. No. 62/358,433 filed Jul. 5, 2016, and U.S. Provisional Ser. No. 62/379,074 filed Aug. 24, 2016; and PCT Patent Application Ser No. PCT/US17/12181 published as WO2017120229A1 on Jul. 13, 2017, which claims priority to all of the aforementioned patent applications; and U.S. Provisional Patent Application Ser. No. 62/560,545, filed Sep. 19, 2017, all of which are incorporated by reference in their entirety herein.

Local Drug and Infusates Infusion Profiles

Acute, semi-acute, and chronic myocardial infarctions result from micro vessel occlusion, microvascular obstruction, catastrophic microvascular collapse all of which may cause both intraluminal plugging by thrombus, cells, proteinaceous materials and relative local myocardial hypotension which in turn decrease capillary size and prevent normal blood flow creating severe ischemia and necrosis. In various embodiments of the present subject matter, the therapy involves infusion protocols and the local agent that is infused.

Various embodiments of the present subject matter provide controlled infusate profiles to treat microvascular collapse resulting from hypertension. It has been found that microvessels can be opened far better utilizing continuous flow as from an external pump than utilizing periodic blood pressure supplied to the arteries via the heart.

For example, an external pump permits continuous application of pressure rather than cyclically varying systolic-diastolic pressure as is typically supplied via the natural cardiac contraction. This can be demonstrated by calculating pressure-time integrals (and using rms equivalent pressure) which show that continuous pressure on the microvasculature to both initially open and maintain opening is far better to maintain flow to the tissue of interest. In some calculations, the flow improvement is greater by a factor of 10 or more for comparable pressures by pump.

Another therapeutic benefit of an external pump is that pressure by the pump may be inserted at supra-physiologic values. For example, in some embodiments of the present subject matter elevated pump pressures are created by continuous or cyclic flow infusion. Infusion into distal microvasculature creates a back pressure via Ohm's law applied to hydrodynamics, $P=Q \times VR$, or pressure equals flow times microvascular resistance, VR.

In various applications of the present subject matter, flow infusion may be placed in a closed loop system to achieve regular and continuous accurate pressure control in "real-time" Markedly elevated intravascular pressures do not have the negative effects that cardiac pressures generated via the left or right ventricle supply. For example, high pressure values (such as 200 mmHg or higher) that are generated by the left ventricle in hypertension put excessive stress and strain on the myocardial wall and thus intense closing pressure on the microvasculature during systole. Moreover, these very high pressures will subject the entire body to hypertension, which even acutely may have profoundly negative clinical consequence. It is thus very difficult to consider raising local myocardial intravascular pressure to open hemodynamically closed capillaries by induction of hypertension.

Conversely, supplying substantially elevated local pressure by catheter can be achieved. In various embodiments of the present subject matter, the proximal vessel is blocked by balloon, thus protecting the body from local hypertension.

In various additional embodiments, the balloon occlusion is not essential. A controlled flow rate will vary the pressure microvascular resistance, and can be adjusted to establish flow to the microvasculature to a level deemed therapeutic, whether or not a drug is included with the infusate.

Infusion pressure at variable infusion rates is a direct measure of microvascular resistance, and as discussed in the Incorporated Applications, is diagnostic regarding the function or dysfunction of the local microvascular structures.

Specifically, elevated pressure supplied by pump is to be used for initial opening of hydrostatically closed capillaries is a 'preparatory pulse' that is utilized to prepare the microvessels to better accept therapeutic solutions. As these capillaries open, a measurable drop in distal infusion pressure will be visualized that reflects decreased hydrodynamic resistance. This pressure change or drop can be measured in real time and be used as feedback to the operator for when hydrostatic opening has occurred. The pressure drop may also be measured and applied to a closed loop control program which adjusts the infusion pressure for desired outcomes. For example, the controller may be adjusted to maintain a constant infusate flow. The controller may be adjusted to maximize the delivery rate of a drug to the microvasculature. The controller may also be used to generate a pulsed pressure waveform to obtain a dynamic measure of microvascular dysfunction, such as MVO.

Infusion of drug containing infusate may clear aggregated and congested cells. Such therapy can affect the platelets, white blood cells, red blood cells, and proteinaceous matter found in obstructed microvasculature during an ischemic event.

Infusion Pulse Sequences

In various embodiments of the present subject matter employing infusate pumps, the delivered controlled infusion has a multiplicity of effects and can be applied in distinct, coupled, and temporally related flow/pressure and/or pulse sequences. The pulse sequences may be controlled manually or by automated control systems which may include a feedback mechanism to stabilize and create precise flow patterns by the pump. Safety of the infusion is enhanced via feedback and closed loop control. For example, if flow creates pressures that are too high, the pump flow can be shut down, decreased, or otherwise limited according to the principles of systems and control theory. In various embodiments, in addition to visualization of real time pressure, resistance, and flow, a visual or verbal alarm may be triggered to alert the operator of over-pressure or under-pressure conditions.

In various embodiments of the present subject matter, the infusion profile may be separated into components. For example, in various approaches, the pulse sequence may include a "preparatory pulse" and "follow-on pulses" or flow infusions.

The "Preparatory Pulse"

A "preparatory pulse" which prepares the microvessels to accept flow, opens them or extends them, while simultaneously delivering drug. The preparatory pulse is a preparation step to open stenosed or occluded microvasculature and in some cases begin drug delivery. The preparatory pulse can be, for example, of high flow or pressure designed to open hydrostatically occluded microvessels. The infusate for this may be a simple liquid such as lactated Ringer's solution, other crystalloid solutions containing beneficial concentrations of sodium, chloride, potassium, glucose, lactate and the like, may in addition be a drug containing solution.

In various embodiments, the duration of this preparatory pulse can be guided by feedback from local, distal pressure measurements and real time observation of myocardium resistance, flow, or cardiac function (pressures and ventricular function measures or intracoronary ECG). In various embodiments, the duration of the preparatory pulse can be limited or discontinued when pressure or resistance calculated drops to a certain predetermined value, or a relative percentage value of initial pressure or resistance.

The preparatory pulse may be high pressure, which is safer than "hypertension" since it is not generated by the ventricle itself and does not generate an elevated intramyocardial pressure that closes microvessels in the elevated pressure clinical syndromes.

In various embodiments, the preparatory pulse may be timed for diastole utilizing the QRS-electrocardiographic complex, or via distal pressure measurement which is cyclic, or any other means to determine lower pressure in the intramural component of the ventricular wall. Moreover, the cyclic natural myocardial contractions and microvessel pulsations themselves provide a potentially useful agitation of diagnostic/therapeutic solutions.

In various embodiments, the preparatory pulse is guided through feedback which tracks a rise in distal pressure that saturates at a given value, indicating that the capillaries in microvasculature have been completely filled and cannot accept more flow without increased pressure in a fixed pattern.

Follow-on Pulses or Flow Infusions

After the preparatory pulse, a subsequent flow infusion is performed to maximize drug delivery to occluded vessels of the microvasculature in comparison to patent or partially patent microvessels. In various embodiments, the follow-on pulses or flow infusion is a controlled-flow infusion with monitoring of distal pressure for purposes of safety and efficacy. If the measured distal pressure rises to unsafe levels flow can be automatically and controllably reduced or discontinued using a computer adjusted algorithm. In various embodiments, the flow can be controllably reduced or discontinued by a manually controlled operator-based system which provides a signal to the operator.

In various embodiments, during the infusion phase, low pressures may be employed for the purposes of generating advantageously the steep increase in microvascular resistance at low pressures. Studies show a natural logarithmic relationship between myocardial flow (Q) and resistance (R), with steep resistance increases as flow rate drops. In various embodiments, this low-flow-low-pressure infusion strategy can more equalize resistance of obstructed microvasculature and patent microvasculature (due to low pressure-low flow infusion). This in turn equalizes these two parallel resistances (obstructed/nonobstructed microvasculature), which thus delivers proportionally and absolutely more flow to occluded or partially occluded microvessels. Sequences of preparation and impulses may be chained and repeated through time.

In various embodiments of the present subject matter, proximal balloon occlusion is part of these preparatory and therapeutic infusion sequences. As the proximal vessel is occluded virtually all pump flow is directed into the distal vessels.

In various embodiments of the present subject matter, partial balloon occlusion is achieved by monitoring distal pressure. Pressure values lying between coronary residual pressure (CRP) and systolic pressure will indicate a partial balloon occlusion, and may be used to keep, in a feedback loop, the vessel in a partially occluded state. Experimental and theoretical modeling studies demonstrate that the infusion-flow relation constitutes a linear system. Because the system is linear, superposition of flows (pump flow and native coronary artery flow) is a viable modality. One advantage of this approach is that the vessel is perfused by a mixture of infusate plus antegrade native (oxygenated) blood, and thus such pulse sequences can be performed for very long times without risking distal myocardial ischemia. Linear superposition of flows in a linear system permit accurate measurement of distal microvascular resistance via requisite infusion pressure via pump, in parallel with native antegrade blood flow.

In various embodiments, dual or higher (e.g. $3\lambda$, $4\times$ or more) flow superposition as described also permits measurement of native flow. In this approach, incremental flow supplied by the pump is added to native flow to provide an incremental pressure rise. Linearity permits distal resistance measurement, which is equal to incremental pressure divided by incremental known controlled flow (from the pump). This known resistance can then be used to calculate native flow.

For example, while pump flow is still running, total flow is the summation of native plus pump flows. If resistance is known, flows can be individually calculated. When the pump flow is discontinued and resistance and residual pressure are known, the native flow can be similarly calculated.

Flow superposition provides additional measurement options. For example coronary artery flow can be measured using methods, such as the following. In various embodiments, a catheter is placed in position, a pressure wire is placed, and flow infusion is begun. The incremental pressure divided by known inserted flow equals resistance. Consequently, total flow is calculated, and native flow is subtraction of total flow minus flow.

Fractional Flow Reserve

Another measurement that can be accomplished using the flow superposition described herein includes the measurement of fractional flow reserve (FFR), a parameter for determining stenosis severity in an epicardial coronary artery. In one embodiment of the present subject matter, a method for measuring FFR is obtained by combinations of the following steps. A flow infusion catheter is delivered proximal to the stenosis. Aortic pressure is measured by guide catheter or by a separate pressure guidewire measures pressure proximal to stenosis. A guidewire with pressure sensing used to cross the stenosis. Incremental flow by a pump through infusion catheter is initiated. An incremental pressure measurement is obtained with a known flow from pump. A stenosis resistance is calculated as pressure drop across stenosis divided by known coronary flow, which may be calculated as total flow minus flow injected flow.

Absolute Myocardial Resistance

Figure 13:
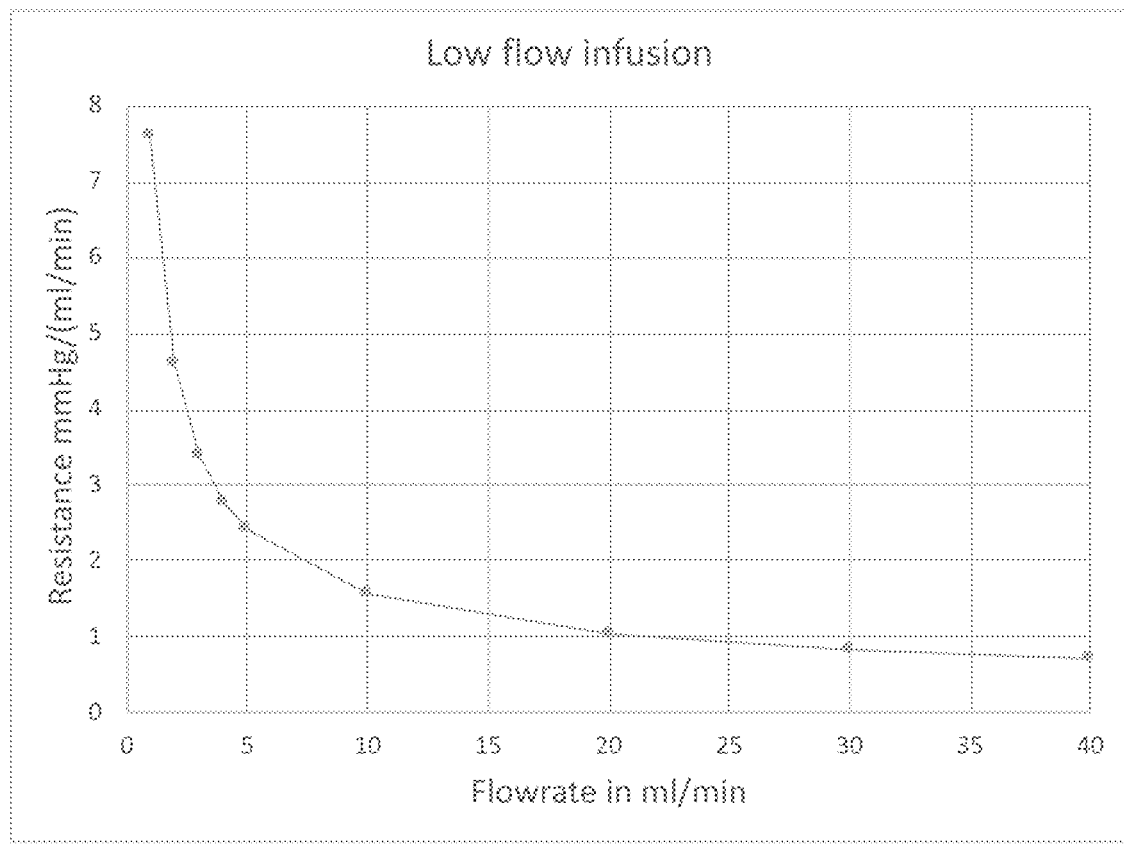
FIG. 13 shows a plot of dynamic myocardial vascular resistance (dMVR) versus flow rate from one study which demonstrates that microcirculation reduces exponentially as flow approaches zero.

In various embodiments, the methods described herein provide an approach for measuring absolute dynamic myocardial vascular resistance (dMVR). The MVR is called "dynamic" as the resistance varies at different flow infusion rates and is exponentially increasing at low flow values. FIG. 13 shows a plot of dynamic myocardial vascular resistance (dMVR) versus flow rate from one study which demonstrates that microcirculation reduces exponentially as flow approaches zero. A calculation utilizing known flow and distal pressure can provide the absolute myocardial resistance (Resistance=Pressure/Flow) at each flow rate. The approach provided herein permits simultaneous distal microvascular resistance and stenosis FFR measurements.

In various embodiments, a constant pressure method will also provide a determination of microvascular resistance in an organ. In one embodiment of the method a pump is utilized either with or without input arterial occlusion (such as by a balloon or other obstructing device). Pressure is monitored as infusion is begun. In various embodiments, an infusion sequence of increasing or decreasing pressure levels is instituted: adjusting the pump rate, monitor back pressure, and that each pressure level record pump flow. This results in and composite set of pressure-flow or within any desired range. The flow is measured at each range, generating a pressure-flow relationship which may be analyzed as per description below.

Determining Microvascular Resistance: Importance of Infusate

One diagnostic method of controlled flow infusion as well as controlled pressure for determining microvascular resistance of any organ can be modified depending on the infusion or infusate that is used as a diagnostic fluid.

Specifically, the importance of whether a fluid is Newtonian or non-Newtonian has important effects on resistance results. Utilization of a Newtonian fluid such as any electrolyte-water-based medical fluid is far superior to blood or other non-newtonian fluids. Utilization of Newtonian fluids, as proven by experiments permit far more accurate demonstration of the microvascular resistance, particularly in the heart, which is highly linear. Utilization of a non-newtonian fluid can make the microvascular resistance of such an organ appeared to be nonlinear. Newtonian fluids also serve as excellent diagnostic solutions and can be used to better control ischemia because they typically lack oxygen. Newtonian fluids also act as a powerful vasodialator, so the heart tissue will not clamp down, further linearizing flow which enhances diagnostic testing and therapeutic perfusion. The use of Newtonian fluids can therefore provide improved pressure response at relatively low flow rates. In various applications, a flow rate as low as 5 mL/minute can give an excellent pressure response which allows for diagnostic and therapeutic applications at pressure levels that are safe for the tissue.

Saline, Lactated Ringer's Solution, or other water based electrolyte fluids are useful for multiple reasons. They provide diagnostic effects and benefits, such as.

(1) Linearity can be proven in the microvasculature.

(2) Low viscosity fluids more easily access distal microvessels, for example in endocardium which represent the terminal capillaries, quite small and subject to changing resistance by virtue of their microscopic size and distal location. Distal location of these vessels creates a secondary issue, being at the far end of the blood pressure cascade, markedly compounding the problem of unimpeded flow during a diagnostic sequence.

(3) Induced controlled hypoxia:

(a.) Electrolyte solutions as noted are also highly advisable because they induce ischemia in the myocardium. Utilization of blood or other oxygen-containing fluids alter diagnostic effects since oxygen maximum vasodilation. A fluid such as crystalloid above contains little to no oxygen and thus fulfills separate roles, not only as a hydrodynamic agent, but also as it is lacking oxygen is an optimal fluid for inducing hypoxic vasodilation.

(b.) Manufactured crystalloid solutions such as lactated Ringer solution moreover provide a very consistent product comparison within a patient or across a population of patients utilization of drugs or blood as it infusate induce substantial errors in determining population values or even within diagnostic runs in the same patient because the diagnostic fluid adversely affects the quality of diagnosis as creates adverse changes in the diagnostic system by its effects on the microvasculature. Consistent across runs and patients. While using blood, blood products or other biologic fluids may have benefits for other diagnoses, the changing nature of blood such as hemoglobin, proteins, micro thrombi and other biologic alterations will induce inaccuracies in the determination of microvascular resistance.

Fluids with high protein content can similarly cause nonlinearities.

In summary, the nonlinearity of the coronary microvasculature are commensurate with the non-Newtonian hydrodynamic characteristics of blood. Experiments have demonstrated that the microvascular resistance is linear when using a Newtonian fluid such as a crystalloid infusate.

Osmolarity

Infusates can be chosen based on a number of parameters, including osmolarity. For example, a hyperosmolar infusate can be used to draw fluid from tissue. For example, an osmolar gradient can be used to reduce or prevent edema in treated tissue.

Accordingly, infusates can be selected based on a number of characteristics, including, but not limited to, how Newtonian the solution is, the percentage of oxygenation of the solution, and the osmolarity of the solution.

Methods of Determining Microvascular Resistance

Methods which determine microvascular resistance in an organ are fraught with inaccuracy by simply dividing infusion pressure by infusion flow. This is especially the case when there is an offset (either constant or variable) pressure which confounds the resistance calculation.

Utilizing a derivative approach across a series of increasing or decreasing flow or pressure stair steps eliminate this offset and generate a highly accurate microvascular resistance measurement. Experiments show that in the case of biologic organs the resistance is highly linear: resulting from plotting the pressure-flow derivative. Curve fitting this line generates accurate record of vascular resistance as the slope, while the intercept is a "zero flow pressure" which is similarly useful for diagnosis as it reflects the DC offset.

In a typical heart, the pressure DC offset results from collateral capillary flow into the distal myocardial bed and is often referred to as the "Coronary Wedge Pressure". This pressure is the most obvious cause of substantial errors in measuring microvascular resistance. It can be eliminated by subtraction but drawbacks to this method is that they require wedge pressure measurement, and moreover me change throughout process.

This derivative-intercept diagnostic method may be used with or without an occlusion device such as a balloon. However, it is likely less accurate when utilizing flowing blood for reasons above, due to the non-Newtonian fluid inducing nonlinearities. Traditional methods of measuring microvascular resistance suffer from this problem the IMR, FFR, CFR and similar indices.

Therapeutic Effects of Infusate Makeup

Therapeutic effects from infusion fluids also benefit from the Newtonian fluid. Not only does this fluid convert a nonlinear system into a linear system, the lower viscosity of crystalloid permits access of therapeutic fluid containing drugs or other therapeutic agents to reach the smallest microvessels of a biologic system. Other therapeutic agents may include those containing oxygen (after for example a diagnostic run has been made without oxygen), all of the therapeutic drugs previously described drug combination such as glucose-insulin-potassium (GIK) which provides a hyperosmolar solution to remove fluid from an edematous biologic organ where the edema is causing interference with normal organ function.

Catheters for Use Diagnostic and Therapeutic Fluid Infusion Using the Constant Flow or Defined Pressure Method The infusion catheter is an important element of accurately determining microvascular function including microvascular resistance. Important features include:

(i.) pressure measurement sensor proximal,
(ii.) capability of placing a pressure measuring guidewire or other sensor distal to the catheter tip, and
(iii.) when infusion is generated by appropriate parameters the P-Q derivative-intercept method is applicable. The vessel obstruction by balloon or other method is not required for this method to be functional.

The pressure measurement capability does not require vessel occlusion since the method is impervious to ongoing constant blood flow. Defined fluid infusion generates a perturbation to this baseline flow in this perturbation is used in the derivative calculation.

Novel Diagnostic Considerations

The vulnerability to ischemia and infarction of the cardiac endocardium is well known. A model for assessing myocardial infarct size can be derived from myocardial microvascular resistance. Anatomic considerations of the distal myocardial microvasculature result in well-defined shapes for ischemic and infarct it myocardial tissue these typically appear as linear endocardial zones which may be in various states of health as defined by levels of ischemia and duration of ischemia. Myocardial infarct size is related to the thickness of the myocardial necrotic wave which progresses from endocardium to epicardial over time.

Diagnostic methods for measuring infarct size by catheter methods can eliminate the need for external imaging procedures such as magnetic resonance imaging.

Microvascular resistance is measured thus down the capillary network from epicardial (where the large epicardial coronary arteries are the blood source) to the Terry distal endocardium which represents the terminal zones of capillary blood supply.

A parallel system analytic method models microvascular resistance as parallel resistances from epicardial to endocardium. A typical analytic approach may be as follows:

(i) a three compartment model consisting of tissue which is 1) healthy, 2) edematous but alive, 3) alive but not functioning, visualized by late get lending enhancement using CMR Techniques, or 4) Dead As Visualized by Microvascular Obstruction in CMR Imaging (ii) this cascade of healthy, dying, or dead tissue is characterized by a three-or more compartment model which utilizes tissue conductivity due to capillary patency or progressive obstruction, the area of the muscle to be studied, and the thickness of the muscle as in the case of cardiac wall thickness, and (iii) systems simultaneous equations can be written that relate microvascular resistance is measured from the epicardial coronary artery to myocardial infarct size utilizing expression $R=\rho L/A$.

Absolute Coronary Artery Collateral Flow

In various embodiments, the methods described herein enable an approach for measuring absolute coronary artery collateral flow. In various embodiments of the present subject matter, coronary artery collateral flow is measured by:
1. Placing a proximal balloon occlusion coronary artery with distal controlled flow infusion via infusion catheter and pressure sensing, as described above;
2. Providing incremental flow infusion with incremental pressure change yields distal myocardial resistance;
3. The balloon remains inflated, pump flow stopped; and
4. Residual pressure with balloon occlusion is measured. The known Coronary Residual Pressure divided by distal resistance equals collateral flow in absolute terms (mmHg/flow (ml)).

These techniques can be used for other organ flow such as, but not limited to, brain, lung, kidney, visceral organs, and distal extremities.

Distal Pressure-Controlled Feedback Loop to Pump Flow

In various embodiments, the controlled flow infusion system may be operated either in open-loop or closed-loop function. In an open-loop function, infusion flow is set at a given value or values predetermined and the pressure distally is measured in an open-loop configuration.

In a feedback configuration, an input signal is used to control the pump and govern flow. One output signal useful for feedback is the peripheral resistance measured by the pressure distal to the balloon. There are multiple applications for the feedback signal. For example, a servo loop can be created so that tight control of pressure, and hence resistance, is possible by maintaining constant distal pressure through flow changes.

In various embodiments, the feedback system provides an important safety mechanism. For example, prevention of over-pressurization due to increased resistance or elevated pump based flow can be prevented by capping the maximum obtainable pressure. This pressure typically will be a physical physiologic pressure such as 90 mmHg or any value pushed by the user. The measured pressure cap can be set beforehand and/or changed dynamically within a procedure.

In various embodiments, the feedback system is used to test the integrity of the endothelium-smooth muscle-vascular tone mechanism. Autoregulation is a natural physiologic mechanism that maintains cardiac flow at a desired value as obtained by multiple physiologic input signals. The integrity of the autoregulation system is testable with methods described herein and utilization in the clinical laboratory implemented by putting setting fixed high-level flow values and observing the vascular response to this high-level flow. Specifically, the microvasculature contracts progressively as it attempts to limit flow. By doing so, the body increases resistance which manifests as an increasing pressure line over time. This experiment has been performed and has been verified and documented in animal models. Several methods for complex physiologic measurements (not currently available) are made possible by this feedback-control loop, including but not limited to the following Autoregulation In embodiments where pressure output is controlled to be relatively constant the input signal to maintain a constant flow, that is the feedback in the control loop, is an accurate representation of resistance and can be used as a measure of dynamic autoregulation. In various embodiments, such measurements can be made in real time. Components of autoregulation include flow sensing by endothelial shear, feedback to smooth muscle in the arterial wall, blood supply to the coronary artery included.

Viability

In various embodiments, myocardial viability is measured as it relates to the magnitude of the phasic pressure that results from myocardial contraction of intra-myocardial coronary capillaries. In various embodiments determination of phasic pressure may be used to determine myocardial viability, either de novo or by a drug infusion such as dopamine, dobutamine, epinephrine or other inotropic pharmacologic agents which will stimulate increased myocardial contractility. This is reflected by increasing phasic resistance signals and increased phasic resistance. Stress tests for viability are interpreted by failure to respond, or a graded level of response to myocardial-capillary constriction on a mechanical basis. Larger or increased pressure pulsations indicate more potent contraction in a fixed and measurable fashion.

Myocardial Stunning or Hibernation and Differentiation from Permanent Cell Death Transient ischemia that 'shocks' the heart muscle physiologically so that it does not contract and hence there is reduced or absent phasic myocardial microvascular resistance. Response to drug suggests viability as phasic resistance grows with drug infusion. Conversely drug infusion nonresponse suggests little or no viability. Similarly, hibernating myocardium may be detected as contractility increasing agents either augment or fail to augment microvascular resistance.

Bubble Filter

In various embodiments of the present controlled feedback system a bubble filter is incorporated into the proximal portion of the infusion system. It comprises a chamber including an inlet followed by passage through a screen of a very hydrophobic material.

Servo Loop Control System

Various embodiments of the present controlled feedback system include a closed loop mode whereby pressure in the distal muscle post balloon occlusion is fed back to the pump-computer system for safety. For example, a predetermined flow safety threshold may be set manually or it may be automatically set and determined by systemic blood pressure at the time of or before vessel occlusion. As another example, the method is adapted to assure that distal pressure as generated by flow will never be excessive. Excessive pressures can be clearly harmful to the distal micro- and epicardial vasculature. As another example, by using a measured or set limit, the pump directing flow can never reach a value which is potentially harmful or dangerous, since the value never exceeds that of physiologic magnitude. A person of skill in the art would understand that other safety advantages are provided by the closed loop system, and the ones stated herein are not intended in an exclusive or exhaustive sense.

Balloon Inflation-Deflation During Infusion

In various embodiments, coronary occlusion balloon inflation and deflation is automated by algorithm and is computer controlled. This allows the system to control balloon inflation and deflation as part of therapeutic or diagnostic sequences and associated parameters, such as infusion pressures, concentrations, permits reoxygenation and fosters long term perfusion. The resistance can be adjusted from low-high by adjustment of balloon inflation. The system allows for intermittent calculation of pressure values and relaxation times following balloon occlusion. It also allows flow and oxygenation to be controlled. The protocol of the present system can be automated for relatively long periods of time. The present system can keep a drug flowing at lower concentrations and can set and adjust mixture and ratios. It is envisioned that the system can adaptively change these settings as needed for any given therapy requirements.

Diagnostics

The present subject matter can be performed using an occlusion balloon, an occlusion balloon with variable inflation levels to modify the degree of occlusion, or without an occlusion balloon (or a deflated occlusion balloon). The resultant distal pressure sensed as the superposition of injected flow and ambient pressure is recorded and used as part of a control algorithm adapted to adjust variables such as one or more of:

Infusion rate and profile of crystalloid fluids (isotonic or otherwise) being delivered:

Transfusion rate of blood or blood products being delivered;

Infusion rate and profile of drugs being delivered, and/or

Amount of occlusion provided by the occlusion device.

The amount of occlusion may vary from full occlusion to partial occlusion to virtually no occlusion by the device inserted in the blood vessel or organ. The timing of the infusions may also be timed to occlusion levels and to heart activity. Other variables may be applied without departing from the scope of the present subject matter.

Waveforms and Flow

The present subject matter includes a programmable system that can provide a constant flow infusion, combined with occlusion control between full, partial and virtually no occlusion delivery states in order to controllably adjust and control one or more of: concentration of delivered fluids, local concentration of delivered and native fluids, flow rate of blood past the occlusive device (e.g., a balloon or other occlusion device), blood supply or resupply to the vessel or organ under therapy, reperfusion therapy, microvascular resistance measurements (which may be obtained simultaneously with other control aspects), delivery of bolus or infusion, ischemia therapy to provide long term local infusion to reduce or avoid ischemia. In various embodiments, these control aspects may be provided simultaneously or serially in various combinations and on an as-needed basis. Other controls may be performed, including modulation of oxygenation levels of infused fluids or of the blood local to the distal end of the catheter device site, cellular therapies, and others, whether singly, serially, or parallel, and in various combinations.

In various embodiments, the system may utilize known waveform insertion, including constant flow as a method to differentiate native resistance changes from inserted flow determination of resistance changes. For example, flow into the microvasculature that results from collateral vasculature is cyclic in nature. By inserting a constant flow waveform that change in pressure/voltage is known due to the inserted flow in comparison with the "native flow" originating from the heart itself. This method will utilize potentially other waveforms besides constant flow and allow interrogation of distal resistance features.

The "coronary residual pressure waveform" originates from internal heart function, and relates to microvascular flow. In the complete absence of antegrade direct coronary arterial flow this flow must be from collateral vessels. Thus, sensing pressure drive against collateral flow, manifest as "zero flow pressure, or "coronary residual pressure" in reality is collateral flow. This is thus a method of directly assessing the state of collateral flow. Importantly collateral flow is believed to be dynamic, changing with cardiovascular conditions, and not fixed in time. Knowledge of this flow will be highly useful clinically and ischemia, and understanding microvascular obstruction.

Utilization of a parameter consisting of distal occlusive/wedge pressure of the coronary artery in relationship to systemic pressure or other pressures within the heart will be useful in assessing macrovascular obstruction. The ratio for example of systemic, not obstructed coronary pressure to obstructed/wedge pressure is a direct assessment of a combination of microvascular obstruction and collateral flow.

To address the microvascular obstruction, in various embodiments, determination of therapeutic efficacy is at least in part indicated by the time course of efficacy via distal flow through the "sponge and bulk mass" comprising the microvasculature. In various embodiments, the system determines the "wavefront of microvascular obstruction."

In various embodiments, the system applies agitation of flow and pressure to enhance microvascular clot lysis via pump starting-stopping in conjunction with balloon inflation-deflation. These physical phenomena will assist in making drug or accessible to lyse the microvascular thrombus.

In various embodiments dIMR or the differential dP/dQ is the instantaneous slope or instantaneous flow through it the coronary artery or microvasculature. This resistance is measured directly as the back pressure in a zero flow situation of the epicardial coronary artery. In the event that microvascular resistance is a linear function of pressure and flow, P/Q is effective and measures resistance directly. Conversely that the differential expression dP/dQ is more generalizable as it measures differential changes in resistance in real-time.

Utilization of the present subject matter is applicable to diagnosis and therapy of the kidney, brain (e.g., treatment or avoidance of stroke) or other neurologic tissues (peripheral nerves, spinal cord), peripheral vasculature, other abdominal viscera including intestine (large or small bowel), pancreas, liver, spleen.

The present subject matter is also used to determine the state of endothelial function of any artery or vein. In various applications, the present subject matter can be used to diagnose and/or treat macro or micro vessel size changes and subsequent flow changes in relationship to stimulus such as hypoxia, electrolyte change, drug injection such as acetylcholine or other endothelial dependent vasodilators.

The present subject matter is also useful for the detection and quantification of the autoregulation of specific biologic tissue regulating optimal flow into and out of that organ as occurs in the heart, brain, kidneys, muscles and others. Infusing flow directly into these organs and quantitative fashions permits quantitation of the organ vascular response to that flow. This is thus a direct quantitation of the intact state of autoregulation, and its magnitude.

The present subject matter is also available for diagnosis and/or therapy using intracardiac electrocardiography, placing a monopole or, bipolar; or multipolar lead within a guidewire to measure injury status of the myocardium as a supplement to determining efficacy of flow infusion to lyse microvascular clot.

The present subject matter is also available for mitigation of reperfusion injury by chemical or physical properties (cold, heat etc.). The present subject matter is also available for injection of lytics normally given intravenously directly into a coronary artery to obtain exquisite control of concentration and markedly enhance concentration for better efficacy.

The present subject matter can provide "algorithmic" infusion, which includes, for example, interspersed with rest periods, changing of amplitudes and timing to enhance infusion and lytic capability.

The present subject matter provides for, among other things. "closing the loop" according to systems analysis and theory, utilizing diagnostics in real time conjunction with therapeutics to understand progress efficacy and judging of procedural completion.

Distal Pressure-Controlled Feedback Loop to Pump Flow

In various embodiments, the controlled flow infusion system may be operated either in open-loop or closed-loop function. In an open-loop function, infusion flow is set at a given value or values predetermined and the pressure distally is measured in an open-loop configuration.

In a feedback configuration, an input signal is used to control the pump and governance flow. One output signal is the peripheral resistance measured by the pressure distal to the balloon. There are multiple applications for the feedback signal. For example, a servo loop can be created so that rigid control of pressure, and hence resistance, is possible by maintaining constant distal pressure through flow changes.

In various embodiments, the feedback system provides an important safety mechanism. For example, prevention of over pressurization due to increased resistance or elevated pump-based flow can be prevented by putting a system cap on the maximum obtainable pressure. This pressure typically will be a physical physiologic pressure such as 90 mmHg or any value pushed by the user. The measured pressure cap can be then used for further diagnosis and therapeutic efficacy determination.

In various embodiments, the feedback system is used to test the integrity of the endothelium-smooth muscle-vascular tone mechanism. Autoregulation is a mechanism that maintains cardiac flow at a desired value as obtained by multiple physiologic input signals. The integrity of the autoregulation system is testable and utilization in the clinical physiology laboratory by putting in a fixed high-level flow and observing the vascular response to this high-level flow. Specifically, the microvasculature contracts progressively in an attempt to limit flow and by doing so increases resistance. This in turn manifests as an increasing pressure over time. This experiment has been done and has been documented several times in the animal model. Several methods for complex physiologic measurements (not currently available) are made possible by this feedback-control loop, including but not limited to the following.

Autoregulation

In embodiments where pressure output is controlled to be relatively constant, the input signal is used to maintain a constant flow as in an inverting input feedback operational amplifier, the feedback in the control loop is an accurate representation of resistance and can be used as a measure of dynamic autoregulation. In various embodiments, such measurements can be made in real time. Components of autoregulation include flow sensing by endothelial shear, feedback to smooth muscle in the arterial wall, blood supply to the coronary artery included.

Viability

In various embodiments, myocardial viability is measured as it relates to the magnitude of the phasic pressure resulting from myocardial contraction of myocardial coronary artery capillaries. In various embodiments to test myocardial viability during the infusion a test drug may be added such as dopamine, dobutamine, epinephrine or other inotropic pharmacologic agents which will stimulate increased myocardial contractility. This is reflected by increasing phasic resistance signals Stress tests for viability are interpreted by failure to respond, or a graded level of response to myocardial-capillary constriction on a mechanical basis. Larger or increased pressure pulsations indicate more potent contraction in a fixed and measurable fashion.

Myocardial Stunning or Hibernation and Differentiation from Permanent Cell Death Stunned or hibernating myocardium is alive, with viable myocardial cells which are NOT contracting at all or are or hypo-contractile due to transient myocardial ischemia or real-time ischemia and lack of myocardial energetics to contract. As viability studies previously are carried out utilizing an inotropic agent stunned or hibernating myocardium is still alive and can recover given the appropriate circumstances of normalization of electrolytes and glucose for physiologic energy. A viable response to drug suggests living and potentially functioning cells as phasic resistance grows with drug infusion. Conversely, drug infusion nonresponse suggests little or no viability Novel Air and Gas Bubble Filter In various embodiments of the present controlled feedback system a bubble filter is incorporated into the proximal portion of the infusion system. It comprises a chamber including an inlet followed by passage through a screen of a very hydrophobic material. In various embodiments, specialized bubble filters are made for this device. These bubble filters have a fine screen of hydrophobic polymer, and placed in a capsule which is in line with the pump flow. Hydrophobicity will not allow bubbles to pass through the screen. High flows can be obtained with this method, and safety against bubbles is maintained.

Valve and Connectors

Valves and connectors made in "block formation" such that a single plug may connect all flows to the proper antegrade source. The devices are indexed so they fit a certain direction the guarantee proper and solid connections.

Various embodiments of the present controlled feedback system include a closed loop mode whereby pressure in the distal muscle post balloon occlusion is fed back to the pump-computer system for safety. For example, a predetermined flow safety threshold may be set manually or it may be automatically set and determined by systemic blood pressure at the time of or before vessel occlusion. As another example, the method is adapted to assure that distal pressure as generated by flow will never be excessive. Excessive pressures can be clearly harmful to the distal micro and epicardial vasculature. As another example, by using a measured or set limit the pump directing flow can never set a value which is potentially harmful or dangerous, since the value never exceeds that of physiologic magnitude. A person of skill in the art would understand that other safety advantages are provided by the closed loop system, and the ones stated herein are not intended in an exclusive or exhaustive sense.

Characterization of Native Microvascular Resistance: Mathematical Representation of Microvascular Resistance Research has demonstrated the benefits of modelling the microvascular resistance at the time of and during therapy as well as prior to therapy to establish a baseline microvascular status. Microvascular resistance is not a single number; it is variable and depends on the flow rate, MVR (Q). Research shows This feature is modelled very well in a closed form approximation using an inverse natural logarithm function with 2 constants $\alpha$ and $\beta$:

$$MVR(Q) = -\alpha \times \ln(Q) + \beta$$

The closed form equation is useful to measure the function quantitatively, is usable in real time, and the constants are a simple method to determine state of the myocardial resistance distal to a coronary balloon or injection catheter at any time. It thus is a method to 1) determine the need for therapy and 2) observe therapeutic effects in real time, and 3) determine when therapy may be discontinued.

Determination of the 2 constants is performed by a step-function infusion at rates varying from 0.1 ml/min up to 50 or more ml/min, and performing nonlinear curve fit methods to the resulting flow step function resistance response.

Balloon Inflation-Deflation During Infusion

In various embodiments, balloon inflation and deflation is automated by algorithm and is computer controlled. That allows the system to control balloon inflation and deflation as it changes other parameters, such as infusion pressures, concentrations, permits reoxygenation and fosters long term perfusion. The resistance can be adjusted from low-high by adjustment of balloon inflation. The system allows for intermittent calculation of Tau, or pressure decay following coronary artery balloon occlusion. It also allows flow and oxygenation to be controlled. The protocol of the present system can be automated for relatively long periods of time. The present system can keep a drug flowing at lower concentrations and can set and adjust mixture and ratios. It is envisioned that the system can adaptively change these settings as needed for any given therapy requirements.

In various embodiments, control of the occlusion balloon is automated utilizing an algorithm to alternately inflate and deflate the balloon at strategic times. For example, during infusion of a drug an algorithm will keep the drug infusion going at a specified level, and the occlusion balloon will be alternatively inflated and deflated rhythmically. Timing of this inflation-deflation will be such that during deflation enough proximal blood will flow into the distal vessel to keep the heart appropriately oxygenated and supplied with appropriate electrolytes.

Inflation-deflation will also agitate the drug solution and permit improved entry into slow or occluded micro channels. It is noted that slow flow will increase microvascular resistance and more perfectly match the flows between open and closed channels. By running a series of progressively increasing and decreasing stepwise flows evidence of this match and improved drug delivery can be obtained the solution of this equilibrium point is a function of parallel resistances by algorithm. These infusion algorithms in a stepwise fashion can be performed in real time, ongoing, and adjusted to optimize flow into the closed channel as these closed channels lower their resistance permit additional flow of drug.

Alternating Balloon Inflation and Deflation Causes Changes in Infusion Pressures In various embodiments, alternating balloon inflation and deflation causes changes in infusion pressures and may change drug concentration. In various embodiments, the system simultaneously permits reoxygenation between occlusion cycles. In various embodiments, the system allows for very long term perfusion. The vessel continues to be perfused and at the same time receives drug for therapeutic alleviation of microvascular obstruction.

In various embodiments, each balloon inflation permits repetitive and nearly constant Tau pressure decay calculation. In various embodiments and applications, this is a secondary and confirmatory measure of microvascular resistance, useful for determining efficacy of drug in enhancing flow. In various embodiments and applications, the process also keeps drug flowing at lower concentrations. It can also set a mixture and a ratio and can change this instantaneously during the infusion Controlled Flow Infusion and Dynamic Coronary Microvascular Function Study Dynamic Coronary microvascular function can be characterized by controlled coronary flow infusion (CoFI, FIG. 1) which is catheter-based, accurate, and yields continuous results in real time. A controlled flow infusion study was performed to characterize microvascular function and dysfunction across a variety of flow rates, including those occurring in clinical syndromes such as STEMI/NSTEMI, microvascular obstruction, no-reflow, and cardiogenic shock.

Figure 10:
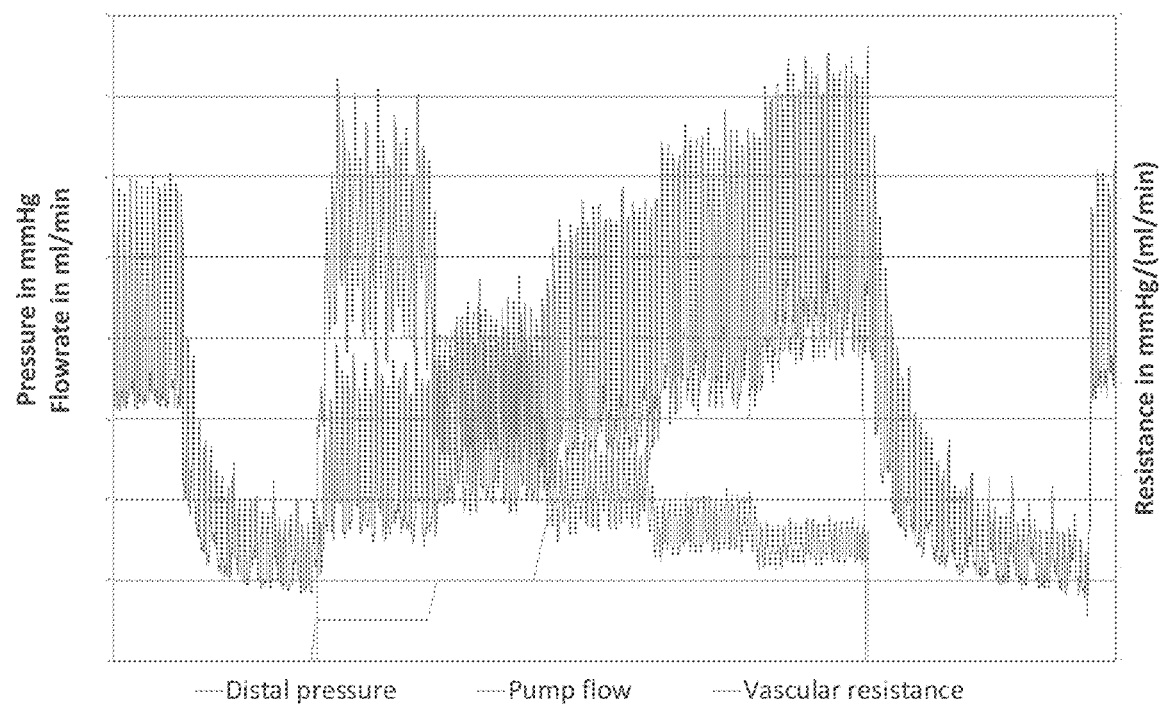
FIG. 10 shows a plot of microvascular resistance, distal pressure and pump flow for a controlled flow infusion performed according to one embodiment of the present subject matter.

Dynamic microvasculature resistance and function was assessed in animal studies using controlled flow infusion (CoFI). An intracoronary catheter with proximal balloon inflation completely blocked antegrade coronary blood flow, and a distal infusion port was used for precise crystalloid delivery via an external pump to the distal coronary microvasculature. Distal intracoronary pressure was measured via pressure wire, yielding the back-pressure derived from the pump-derived microvasculature flow. Pump flow infusion was a step function with ranges across a broad flow range. Time dependent pump flow, Q(t) and distal pressure P(t) were linearly related, according to the equation $P(t)=R(t)\times Q(t)+P0$, where R is resistance, and P0 is a linear constant. Dynamic microvascular resistance was thus:

$$R(t)=dP(t)/dQ(t)+R_0$$

where $R_0$ is the Zero Flow Resistance dhMVR was evaluated at across a broad flow range, 0-40 ml/min in steps of 5, 10, 20, 30 and 40 ml/min for 15 sec each. Coronary pressure waveforms at each flow step showed both tonic and phasic microvascular resistance, derived from basal tone and cyclic intramyocardial compression (FIG. 10). FIG. 10 shows a plot of microvascular resistance, distal pressure and pump flow for a controlled flow infusion performed according to one embodiment of the present subject matter.

FIG. 10 shows resulting real time dMVR (vascular resistance) and coronary pressure (distal pressure) for a controlled flow infusion performed according to one embodiment of the present subject matter dMVR varied inversely and linearly with infused flow ranges from 3.17 (5 ml/min) to 0.85 (40 ml/min). dMVR was derived from the controlled flow step function (5, 10, 20, 30, and 40 ml/min).

Figure 11:
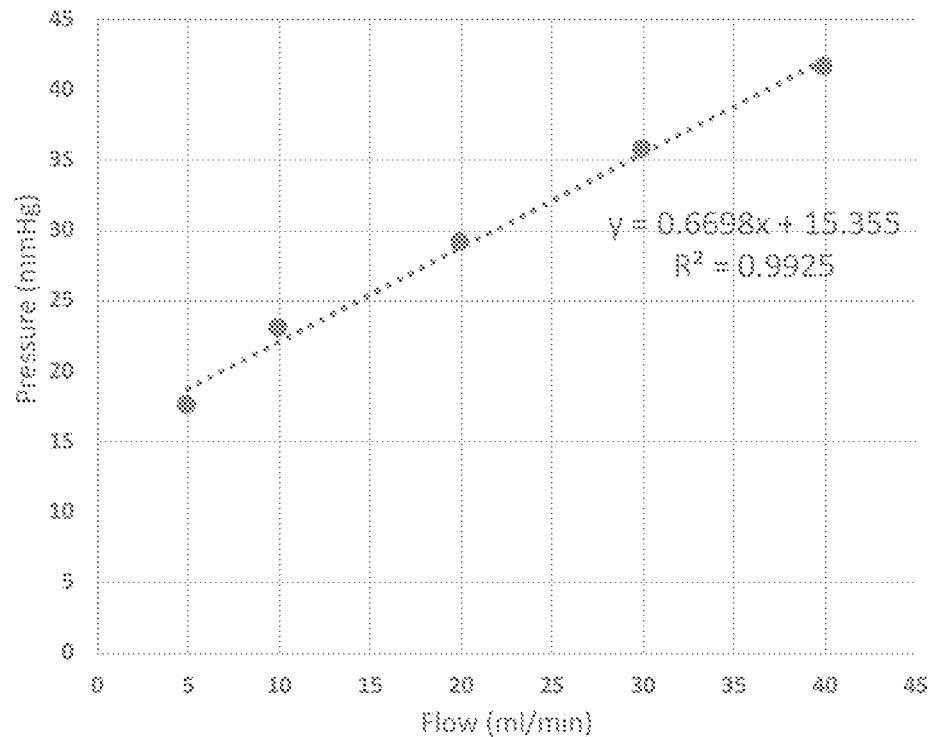
FIG. 11 shows a plot of coronary pressure versus pump flow for a controlled flow infusion performed according to one embodiment of the present subject matter.

FIG. 11 shows a plot of coronary pressure versus pump flow for a controlled flow infusion performed according to one embodiment of the present subject matter. The pressure-flow relationship is highly linear across flow rates 5-40 ml/min. dMVR uniformly varied inversely and linearly with infused flow ranges across all subjects. The linearity of the relationship is reflected by $R^2=0.9925$. The mean dMVR was 0.53±0.14 mWU for the mid-LAD location.

As CoFI flow was decreased below 10-15 ml/min, mean microvascular resistance increased to mean 1.67±0.8 mWU, a 3-fold (3.06±0.89) increase. Pressure corresponding to this flow threshold was mean ~25-30 mmHg and peak systolic ~55 mmHg).

The results of this study confirm that controlled flow infusion is a novel catheter based method for determining dynamic microvascular resistance. It is rapid, simple, accurate and yields real time measurement if desired. In this application, microvascular resistance is dynamic and fundamentally linear across physiologic pressure and flow. This contrasts with prior studies showing a nonlinear P-Q microvascular relationship, which is likely due to the non-Newtonian nature of blood, and physiologic mechanisms such as autoregulation.

This study has important implications for clinical practice. During acute coronary syndromes (STEMI/NSTEMI/Shock), coronary occlusion limits blood flow to the distal microvasculature and thus induces ischemia based on low flow. Low flow arises from low intraluminal pressure, in turn causing microvascular instability and dysfunction, with rapid and marked resistance increase. This data suggest this phenomenon begins at 50-60 mmHg (systolic), correlating well with clinical experience. Prevention and therapy of microvascular dysfunction may be alleviated by reinstating normal pressure and flow, assisted by both hydrodynamic and pharmacologic means.

Real Time Absolute Dynamic Microvascular Resistance Using Controlled Flow Infusion Study Microvascular dysfunction distal to coronary artery occlusion in STEMI is common. The effects are poorly understood despite years of study, and many failed therapeutic strategies. Controlled coronary flow infusion (CoFI, FIG. 1) is a novel catheter-based technique capable of accurately and continuous microvascular function assessment and in real time. This preclinical study used CoFI to explore STEMI effects on microvasculature function in a porcine model.

STEMI was induced in 12 subject pigs by LAD balloon occlusion for 90 minutes. CoFI assessed the distal microvasculature using LAD intracoronary balloon occlusion to block antegrade flow, with simultaneous crystalloid infusion of the distal coronary microvascular bed via step function controlled digital pump. Coronary Back-pressure from the controlled step infusion flow Q(t) was measured by pressure wire. This study characterized the LAD microvasculature across a large dynamic flow range, 0-40 ml/min in steps of 5, 10, 20, 30 and 40 ml/min for 15 sec each.

Absolute dynamic microvascular resistance (dMVR) was derived as the time dependent slope of the function P(t)/Q(t):

$$R(t) = dP(t)/dQ(t) + R_0$$

where R(t) is time dependent resistance, P(t) is coronary pressure, Q(t) is $R_0$ is the constant Zero Flow Resistance. Coronary pressure waveforms at each flow step showed both tonic and phasic microvascular resistance, derived from basal tone and cyclic intramyocardial compression (FIG. 11). FIG. 11 shows a plot of coronary pressure versus pump flow for a controlled flow infusion performed according to one embodiment of the present subject matter.

Figure 12:
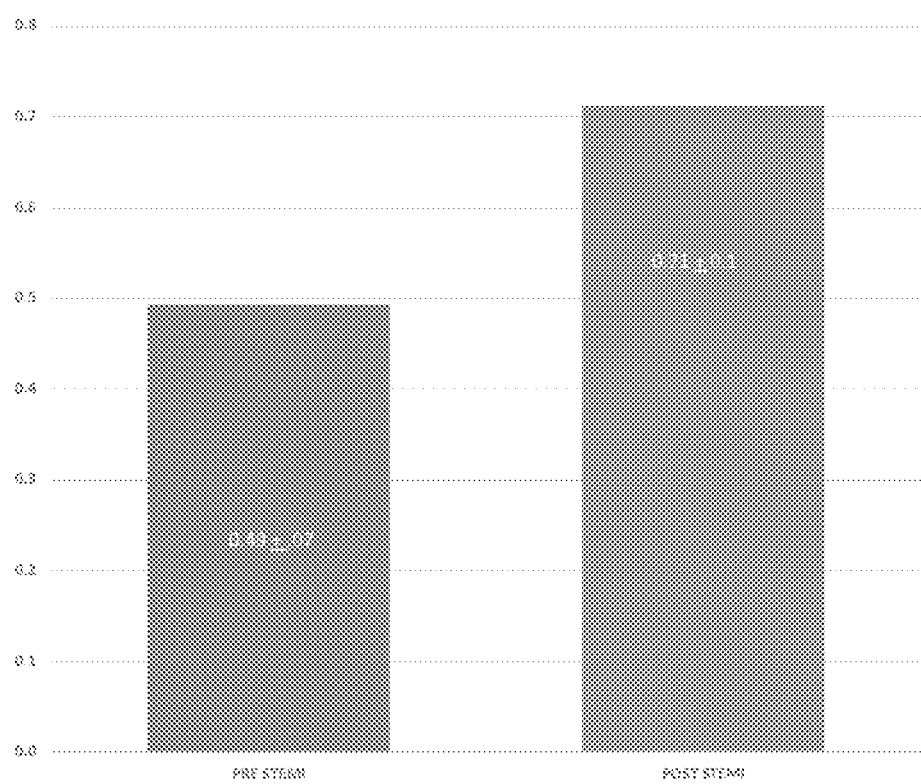
FIG. 12 shows a chart of microvascular resistance pre- and post-STEMI from one study.

FIG. 12 shows a chart of microvascular resistance pre- and post-STEMI from one study. Microvascular Resistance dMVR derived from the pressure-flow relationships pre- and post-STEMI showed a marked increase in post-STEMI microvascular resistance (mWU), 0.49±0.07 vs 0.71±0.1 mean, a 44% increase.

Dynamic myocardial vascular resistance (dMVR) was also studied. FIG. 13 shows a plot of dynamic myocardial vascular resistance (dMVR) versus flow rate from one study which demonstrates that microcirculation reduces exponentially as flow approaches zero.

Microvascular resistance increased substantially in anterior wall STEMI was efficiently and safely measured by controlled flow infusion. Severe microvascular dysfunction and collapse at low perfusion pressure may be profound in both normal and infarct myocardial territories. This dynamic resistance may explain serious clinical instability in STEMI patients, predisposing them to cardiogenic shock and no-reflow syndromes. Therapeutic catheter-based strategies may be devised to limit microvascular dysfunction to prevent potentially serious early and late complications.

Dynamic microvascular resistance may explain serious clinical instability in STEMI patients, predisposing them to cardiogenic shock and no-reflow syndromes. Therapeutic catheter-based strategies may be devised to limit microvascular dysfunction to prevent potentially serious early and late complications.

EXAMPLES

Some aspects of the present subject matter include one or more of the following:

Example 1 of the present subject matter includes a method for treatment of microvascular dysfunction in an organ or limb using apparatus for providing controlled flow infusion of at least a first solution to a vessel for assessment and diagnosis of microvascular function and for providing a second solution to the vessel for therapeutic benefit of the microvascular function.

Example 2 includes the subject matter of Example 1, wherein the first solution is a Newtonian fluid chosen to enhance linearity of the flow to better assess microvascular parameters.

Example 3 includes the subject matter of Example 1, wherein the first solution lacks oxygenation to control hypoxia.

Example 4 includes the subject matter of Example 1, wherein the first solution lacks oxygenation to vasodialate the microvasculature.

Example 5 includes the subject matter of Example 1, wherein the first solution is a crystalloid.

Example 6 includes the subject matter of any one or any combination of Examples 1-5 and further includes: infusing the first solution and the second solution to the vessel using a computerized diagnostic and infusion system; and electronically preforming the assessment of microvascular function automatically in real-time using the computerized diagnostic and infusion system.

Example 7 includes the subject matter of any one or any combination of Examples 1-6 and further includes applying the method to treat acute myocardial infarction, wherein the controlled flow infusion comprises a controlled coronary flow infusion (CoFI).

Example 8 includes the subject matter of Example 7 and further includes applying the method to treat microvascular obstruction (MVO).

Example 9 includes the subject matter of Example 8, wherein the therapeutic benefit comprises elimination of microvascular clot and debris.

Example 10 includes the subject matter of any one or any combination of Examples 1-9, wherein the assessment and diagnosis of microvascular function comprises measuring a pressure in the vessel.

Example 11 includes the subject matter of Example 10, wherein measuring the pressure in the vessel comprises measuring the pressure resulting from superposition of infused and native fluids.

Example 12 includes the subject matter of Example 10, wherein the assessment and diagnosis of microvascular function comprises determining microvascular resistance.

Example 13 includes the subject matter of any one or any combination of Examples 1-12, wherein the treatment of microvascular dysfunction comprises: applying a pulse of the first solution at defined, elevated at least one of pressures or flows to open microvessels; and applying a defined flow of the second solution at defined, elevated at least one of pressures or flows to reduce, avoid, or eliminate ischemia and necrosis of tissue of the organ.

Example 14 of the present subject matter includes an apparatus for measuring microvascular dysfunction in an organ or limb having a vessel and microvasculature connected to the vessel. The apparatus includes: an infusion catheter comprising a plurality of expandable structures connected to one or more lumens of the catheter to remotely control expansion and contraction of the expandable structures and at least one infusion lumen for delivery of infusate to the catheter proximal the expandable structures; an infusion pump in communication with the infusion lumen of the infusion catheter, a plurality of separate solutions in separate reservoirs in communication with the infusion pump; and a computerized controller configured to communicate with the infusion pump and to control operation of the infusion pump to perform controlled flow infusion of at least a first solution of the plurality of solutions to the infusion lumen of the catheter and a second solution of the plurality of solutions to the infusion lumen of the catheter, wherein the first solution is associated with assessment of microvascular function and the second solution is associated with changes to microvascular function.

Example 15 includes the subject matter of Example 14, wherein the first solution is a solution that is associated with dilation of microvasculature.

Example 16 includes the subject matter of Example 15, wherein the first solution is a Newtonian fluid chosen to enhance linearity of the flow to better assess microvascular parameters.

Example 17 includes the subject matter of Example 15, wherein the first solution lacks oxygenation to control hypoxia.

Example 18 includes the subject matter of Example 15, wherein the first solution lacks oxygenation to vasodilate the microvasculature.

Example 19 includes the subject matter of Example 15, wherein the first solution is a crystalloid.

Example 20 includes the subject matter of Example 15, wherein the second solution is a solution for reducing, avoiding, or eliminating ischemia and necrosis of tissue of the organ or limb.

Example 21 includes the subject matter of Example 20, wherein the second solution is a solution for dissolution of a microvascular clot or debris in a heart, Example 22 includes the subject matter of any one or any combination of Examples 15-21, wherein the controller is programmed to cause the pump to: apply a pulse of the first solution at defined, elevated at least one of pressures or flows; and apply a defined flow of the second solution at defined, elevated at least one of pressures or flows.

Example 23 includes the subject matter of any one or any combination of Examples 14-22, wherein the controller is configured to perform assessment of microvascular function automatically in real-time.

Example 24 includes the subject matter of Example 23 and further includes a pressure sensor configured to sense a pressure in the vessel, wherein the controller is configured to perform the assessment of microvascular function using the sensed pressure.

Example 25 includes the subject matter of Example 24, wherein the pressure sensor is attached to the infusion catheter.

Example 26 includes the subject matter of any one or any combination of Examples 14 and 25, wherein the controller is configured to perform assessment of microvascular function using the sensed pressure resulting from superposition of infused and native fluids.

Example 27 includes the subject matter of any one or any combination of Examples 14-26, wherein the controller is configured to determine a microvascular resistance and to assess microvascular function using the determined microvascular resistance.

Example 28 includes the subject matter of any one or any combination of Examples 14-27, wherein the controller is configured to control the pump to perform controlled coronary flow infusion (CoFI).

Example 29 includes a method for treatment of microvascular obstruction in an organ or limb using a controlled flow infusion to a site and pressure measurement response of the resulting superposition of infused and native fluids.

Example 30 includes the subject matter of Example 29, including applying a first fluid pulse at an elevated pressure to open microvessels, and applying a constant flow of infusate at a second pressure, lower than the elevated pressure, to treat the microvascular obstruction and to reduce or avoid ischemia and avoid necrosis of organ tissue.

Example 31 includes the subject matter of Example 29, including calculating the microvascular resistance over a flow range which in combination constitutes a dynamic microvascular resistance at different flow rates.

Example 32 includes the subject matter of Example 31, including applying a first fluid pulse at an elevated pressure to open microvessels; applying a constant flow of infusate at a second pressure, lower than the elevated pressure, to reduce or avoid ischemia; and using the calculated microvascular resistance to define the status of the microvasculature.

Example 33 of the present subject matter includes a method to infuse therapeutic agents to the distal microcirculation during native vessel occlusion at physiologic adapted infusion rates using the already measured values before vessel occlusion, the dynamic microvascular resistance or other physiologic values such as intracoronary ECG to guide the infusion rate and infusion slopes.

Example 34 includes the subject matter of Example 33 in an automated feedback loop to control the timing of the occlusion balloon to optimize the therapeutic effect.

Example 35 includes the subject matter of Example 33 in a non-automated feedback loop to allow an operator to manually control the timing of the occlusion balloon to optimize the therapeutic effect.

Example 36 of the present subject matter includes a method to use the slope of the dynamic microvascular resistance in an automated feedback loop to control the infusion rate, drug selection and/or the timing of the balloon inflation/deflation.

Example 37 of the present subject matter includes a method to use the dynamic microvascular resistance absolute value and relative change over time in an automated feedback loop to control the infusion rate, drug selection and/or the timing of the balloon inflation/deflation.

Example 38 of the present subject matter includes a method to use the intracoronary ECG ST-segment elevation absolute value and relative change in an automated feedback loop to control the infusion rate, drug selection and/or the timing of the balloon inflation/deflation.

Example 39 includes the subject matter of Examples 36, 37, and 38 including to allow the user to manually control the infusion rate, drug selection and/or timing of the balloon inflation/deflation.

The foregoing aspects and examples are not limiting or exclusive, and the scope of the present subject matter is to be determined by the specification as a whole, including the claims and drawings.

The above description includes references to the accompanying drawings, which form a part of the detailed description. The drawings show, by way of illustration, varying embodiments in which the invention can be practiced. The application also refers to "examples." Such examples can include elements in addition to those shown or described. The foregoing examples are not intended to be an exhaustive or exclusive list of examples and variations of the present subject matter.

Method aspects and examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The scope of the invention should be determined with reference to the appended claims, along with the full scope of equivalents to which such claims are entitled.

What is claimed is:

1. A method for measuring microvascular dysfunction in an organ or limb, the method comprising:
providing an apparatus for providing controlled flow infusion of at least a first solution to a portion of a vessel for assessment of microvascular function, the apparatus comprising a pressure sensor, a catheter having an infusion lumen configured to deliver infusate, an expandable structure disposed on the catheter, an infusion pump in communication with infusion lumen of the catheter, and a controller in communication with the infusion pump and the pressure sensor, wherein the infusate comprises the first solution;
expanding the expandable structure;
directing the infusion pump using the controller to deliver the first solution via the infusion lumen in a stepwise manner, the first solution delivered in a first step having a first flow rate, followed by a second step having a second flow rate;
receiving signals from the pressure sensor at the controller, the signals indicative of a first pressure response while the first solution is being delivered at the first flow rate and a second pressure response while the first solution is being delivered at the second flow rate;
determining a linear pressure-flow relationship based on the first flow rate, the first pressure response, the second flow rate, and the second pressure response; and
determining a dynamic microvascular resistance based on the linear pressure-flow relationship.

2. The method of claim 1, wherein the first solution is a Newtonian fluid chosen to enhance linearity of the flow to better assess microvascular parameters.

3. The method of claim 1, wherein the first solution lacks oxygenation.

4. The method of claim 1, wherein the first solution is a water based electrolyte fluid.

5. The method of claim 1, wherein the first solution is a crystalloid.

6. The method of claim 1, wherein the infusate further comprises a second solution configured to provide a therapeutic benefit to the microvascular function.

7. The method of claim 6, further comprising applying the method to treat acute myocardial infarction.

8. The method of claim 7, further comprising applying the method to treat microvascular obstruction (MVO).

9. The method of claim 8, wherein the therapeutic benefit comprises elimination of microvascular clot and debris.

10. The method of claim 1, wherein directing the infusion pump with the controller to deliver the first solution in a stepwise manner comprises directing the infusion pump with the controller to deliver infusate in a series of decreasing steps.

11. The method of claim 1, wherein the first solution is delivered in a third step having a third flow rate, the third step occurring after the second step, and
wherein the second flow rate is greater than the first flow rate, and the third flow rate is greater than the second flow rate.

12. The method of claim 11, wherein a first difference in magnitude between the first flow rate and the second flow rate is the same as a second difference in magnitude between the second flow rate and the third flow rate.

13. The method of claim 11, wherein a first difference in magnitude between the first flow rate and the second flow rate is different than a second difference in magnitude between the second flow rate and the third flow rate.

14. An apparatus for measuring microvascular dysfunction in an organ or limb having a vessel and microvasculature connected to the vessel, the apparatus comprising:
an infusion catheter comprising an expandable structure connected to an inflation lumen of the catheter to control expansion and contraction of the expandable structure and an infusion lumen for delivery of infusate to the vessel;
a pressure sensor configured to be positioned in the vessel;
an infusion pump in communication with the infusion lumen of the infusion catheter; and
a computerized controller in communication with the infusion pump and the pressure sensor, the computerized controller configured to control operation of the infusion pump to perform a time-dependent flow of the infusate and to receive signals from the pressure sensor indicative of time-dependent pressure measurements, wherein the infusate comprises a first solution; and
wherein the time-dependent flow comprises a first step having a first flow rate, followed by a second step having a second flow rate,
wherein the time-dependent pressure measurements comprise a first pressure response associated with the first flow rate, and a second pressure response associated with the second flow rate,
wherein the computerized controller is configured to determine a linear pressure-flow relationship based on the time-dependent pressure and the time-dependent flow, and
wherein the computerized controller is further configured to determine a dynamic microvascular resistance based on the linear pressure-flow relationship.

15. The apparatus of claim 14, wherein the first solution is a solution that is associated with dilation of the microvasculature.

16. The apparatus of claim 15, wherein the infusate comprises a second solution and the second solution is a solution for reducing, avoiding, or eliminating ischemia and necrosis of tissue of the organ or limb.

17. The apparatus of claim 16, wherein the controller is programmed to cause the pump to:
   apply a pulse of the first solution at defined, elevated at least one of pressures or flows; and
   apply a defined flow of the second solution at defined, elevated at least one of pressures or flows.

18. The apparatus of claim 17, wherein the controller is configured to determine the dynamic microvascular resistance automatically in real-time.

19. The apparatus of claim 14, wherein the pressure sensor is disposed on the infusion catheter.

20. The apparatus of claim 14, wherein the pressure sensor is disposed on a guidewire.

\* \* \* \* \*